US012426799B2

United States Patent
Papini

(10) Patent No.: US 12,426,799 B2
(45) Date of Patent: Sep. 30, 2025

(54) DETERMINATION OF CATHETER SHAPE

(71) Applicant: St. Jude Medical, Cardiology Division, Inc., St. Paul, MN (US)

(72) Inventor: Ilan Meir Papini, Haifa (IL)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 1197 days.

(21) Appl. No.: 17/237,279

(22) Filed: Apr. 22, 2021

(65) Prior Publication Data

US 2021/0330213 A1    Oct. 28, 2021

Related U.S. Application Data

(60) Provisional application No. 63/014,453, filed on Apr. 23, 2020.

(51) Int. Cl.
*A61B 5/00*    (2006.01)
*A61B 5/06*    (2006.01)

(52) U.S. Cl.
CPC .............. *A61B 5/063* (2013.01); *A61B 5/062* (2013.01); *A61B 5/6852* (2013.01)

(58) Field of Classification Search
CPC ....... A61B 5/063; A61B 5/062; A61B 5/6852; A61B 2562/0209; A61B 2562/0223;
(Continued)

(56) References Cited

U.S. PATENT DOCUMENTS 6,233,476 B1    5/2001  Strommer et al.
6,498,944 B1    12/2002 Ben-Haim et al.
(Continued)

FOREIGN PATENT DOCUMENTS

CN     1903122 A    1/2007
CN   107750148 A    3/2018
(Continued)

OTHER PUBLICATIONS

"Communication pursuant to Article 94(3) EPC Received mailed on Jul. 5, 2023", 10 Pages.
(Continued)

*Primary Examiner* — Joel Lamprecht
(74) *Attorney, Agent, or Firm* — Billion & Armitage

(57) ABSTRACT

Embodiments of the present disclosure include a method for determining a shape of a catheter. The method can include receiving a plurality of impedance measurements from a plurality of electrodes disposed on a flexible tip portion of the catheter. The method can include receiving a magnetic position measurement from a magnetic position sensor disposed on a shaft of the catheter. The method can include determining a relationship between each of the plurality of electrodes disposed on the flexible tip portion of the catheter, based on the impedance measurements received from the plurality of electrodes. The method can include predicting a shape of the flexible tip portion of the catheter, based on the determined relationship between each of the plurality of electrodes disposed on the flexible tip portion of the catheter. The method can include determining a shape of the catheter, based on the magnetic position measurement and the predicted shape of the flexible tip portion.

15 Claims, 14 Drawing Sheets

(58) Field of Classification Search
CPC ... A61B 5/6855; A61B 5/6856; A61B 5/6857; A61B 5/6859; A61B 5/0538
See application file for complete search history.

(56) References Cited

U.S. PATENT DOCUMENTS

| | | | |
|---|---|---|---|
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 7,885,707 B2 | 2/2011 | Hauck | |
| 8,636,718 B2 | 1/2014 | Sela et al. | |
| 9,326,702 B2 | 5/2016 | Eichler et al. | |
| 9,901,303 B2 | 2/2018 | Olson | |
| 10,758,137 B2 | 9/2020 | Deno et al. | |
| 10,918,307 B2 | 2/2021 | Olson et al. | |
| 2007/0016007 A1* | 1/2007 | Govari | A61B 5/063 600/424 |
| 2007/0060833 A1 | 3/2007 | Hauck | |
| 2008/0275369 A1* | 11/2008 | Fandriks | A61B 5/1107 600/593 |
| 2018/0296111 A1 | 10/2018 | Deno et al. | |
| 2020/0001048 A1* | 1/2020 | Oren | G06T 7/70 |

FOREIGN PATENT DOCUMENTS

| | | | |
|---|---|---|---|
| CN | 107771055 A | 3/2018 | |
| EP | 1743575 A2 | 1/2007 | |
| JP | 2007021218 A | 2/2007 | |
| JP | 2018-519046 A | 7/2018 | |
| WO | 2014/141113 A2 | 9/2014 | |
| WO | 2016/205809 A1 | 12/2016 | |
| WO | WO-2016205807 A1 * | 12/2016 | A61B 18/1492 |
| WO | 2017/177121 A1 | 10/2017 | |

OTHER PUBLICATIONS

"Notice of Reasons for Rejection Mailed on Sep. 26, 2023", 3 Pages.
"Communication Pursuant to Article 94(3) EPC Mailed on Jul. 22, 2024", 13 Pages.
"Non- Final Office Action mailed on Sep. 14, 2024", 25 Pages.
"Second Office Action for CN Application 202180029806.1; mailed on Mar. 17, 2025", 23 Pages.

* cited by examiner

120

- 122 — RECEIVING A PLURALITY OF IMPEDANCE MEASUREMENTS FROM A PLURALITY OF ELECTRODES DISPOSED ON A FLEXIBLE TIP PORTION OF THE CATHETER
- 124 — RECEIVING A MAGNETIC POSITION MEASUREMENT FROM A MAGNETIC POSITION SENSOR DISPOSED ON A SHAFT OF THE CATHETER
- 126 — DETERMINING A RELATIONSHIP BETWEEN EACH OF THE PLURALITY OF ELECTRODES DISPOSED ON THE FLEXIBLE TIP PORTION OF THE CATHETER, BASED ON THE IMPEDANCE MEASUREMENTS RECEIVED FROM THE PLURALITY OF ELECTRODES
- 128 — PREDICTING A SHAPE OF THE FLEXIBLE TIP PORTION OF THE CATHETER, BASED ON THE DETERMINED RELATIONSHIP BETWEEN EACH OF THE PLURALITY OF ELECTRODES DISPOSED ON THE FLEXIBLE TIP PORTION OF THE CATHETER
- 130 — DETERMINING A SHAPE OF THE CATHETER, BASED ON THE MAGNETIC POSITION MEASUREMENT AND THE PREDICTED SHAPE OF THE FLEXIBLE TIP PORTION

*FIG. 3*

DETERMINATION OF CATHETER SHAPE

CROSS-REFERENCE TO RELATED APPLICATIONS

This application claims the benefit of U.S. provisional application No. 63/014,453, filed 23 Apr. 2020, which is hereby incorporated by reference as though fully set forth herein.

BACKGROUND a. Field of the Invention

The present disclosure relates generally to the determination of a catheter shape.

b. Background Art

Medical devices, catheters, and/or cardiovascular catheters, such as electrophysiology catheters can be used in a variety of diagnostic, therapeutic, mapping and/or ablative procedures to diagnose and/or correct conditions such as atrial arrhythmias, including for example, ectopic atrial tachycardia, atrial fibrillation, and atrial flutter. A medical device can be threaded through a vasculature of a patient to a site where the diagnostic, therapeutic, mapping, and/or ablative procedure to diagnose and/or correct the condition is performed.

Sensors (e.g., electrodes, magnetic positioning sensors) can be placed on the medical device, which can receive signals that are generated proximate to the patient from a device. Based on the received signals, an orientation and/or position of the medical device within a heart can be computed.

One technique for determining the position and orientation of a catheter within a body is by tracking a plurality of sensors on the catheter using a position sensing and navigation system (sometimes called a location mapping system). The sensors can include electrodes disposed on the catheter, which can provide voltage measurements associated with their exposure to an electrical field generated through excitation of pairs of electrodes on an outer surface of the body. Voltage measurements on the catheter electrodes can then be used to determine the position and orientation of the catheter electrodes within a coordinate system of the position sensing and navigation system. Other exemplary position sensing and navigation systems include magnetic systems.

In order to provide information to clinicians about the position and orientation of the catheter, the determined position and orientation of the catheter sensors is often used to render an image of the catheter relative to surrounding tissues, including heart tissues. One drawback to conventional systems, however, is that the determined position and orientation of the catheter sensors can include errors due to errors associated with data received from the catheter electrodes. In an example, the position of the catheter electrodes can be affected due to shift and/or drift. For instance, impedance can slowly drift or even undergo transient shifts due to, for example, a change in medication leading to drift and/or shift in the detected position of the medical device. Furthermore, the data received from the catheter electrodes can be non-linear in nature, which can make it difficult to determine a position of the catheter in linear space when using the non-linear data. As a result, a rendered shape of the catheter, which is based on the determined position of the catheter electrodes can be distorted from its true mechanical shape, as a result of the errors and non-linear nature of the data received from the catheter electrodes.

SUMMARY

Embodiments of the present disclosure include a method for determining a shape of a catheter. The method can include receiving a plurality of impedance measurements from a plurality of electrodes disposed on a flexible tip portion of the catheter. The method can include receiving a magnetic position measurement from a magnetic position sensor disposed on a shaft of the catheter. The method can include determining a relationship between each of the plurality of electrodes disposed on the flexible tip portion of the catheter, based on the impedance measurements received from the plurality of electrodes. The method can include predicting a shape of the flexible tip portion of the catheter, based on the determined relationship between each of the plurality of electrodes disposed on the flexible tip portion of the catheter. The method can include determining a shape of the catheter, based on the magnetic position measurement and the predicted shape of the flexible tip portion.

Embodiments of the present disclosure include a system for determining a shape of a catheter. The system can include a processor and a memory storing instructions on a non-transitory computer-readable medium, wherein the instructions executable by the processor to receive a plurality of raw impedance measurements from a plurality of electrodes disposed on a flexible tip portion of the catheter. The system can include instructions executable by the processor to receive a magnetic position measurement from a magnetic position sensor disposed on a shaft of the catheter. The system can include instructions executable by the processor to determine an angle between each of the plurality of electrodes disposed on the flexible tip portion of the catheter, based on the raw impedance measurements received from the plurality of electrodes. The system can include instructions executable by the processor to predict a shape of the flexible tip portion of the catheter, based on the determined angle between each of the plurality of electrodes disposed on the flexible tip portion of the catheter. The system can include instructions executable by the processor to shift a determined location of the flexible tip portion of the catheter based on the magnetic position sensor measurement. The system can include instructions executable by the processor to determine the shape of the catheter using the shifted location of the flexible tip portion of the catheter.

BRIEF DESCRIPTION OF THE DRAWINGS

FIG. 3 depicts a method for determining a shape of a catheter, in accordance with embodiments of the present disclosure.

DETAILED DESCRIPTION

Figure 1:
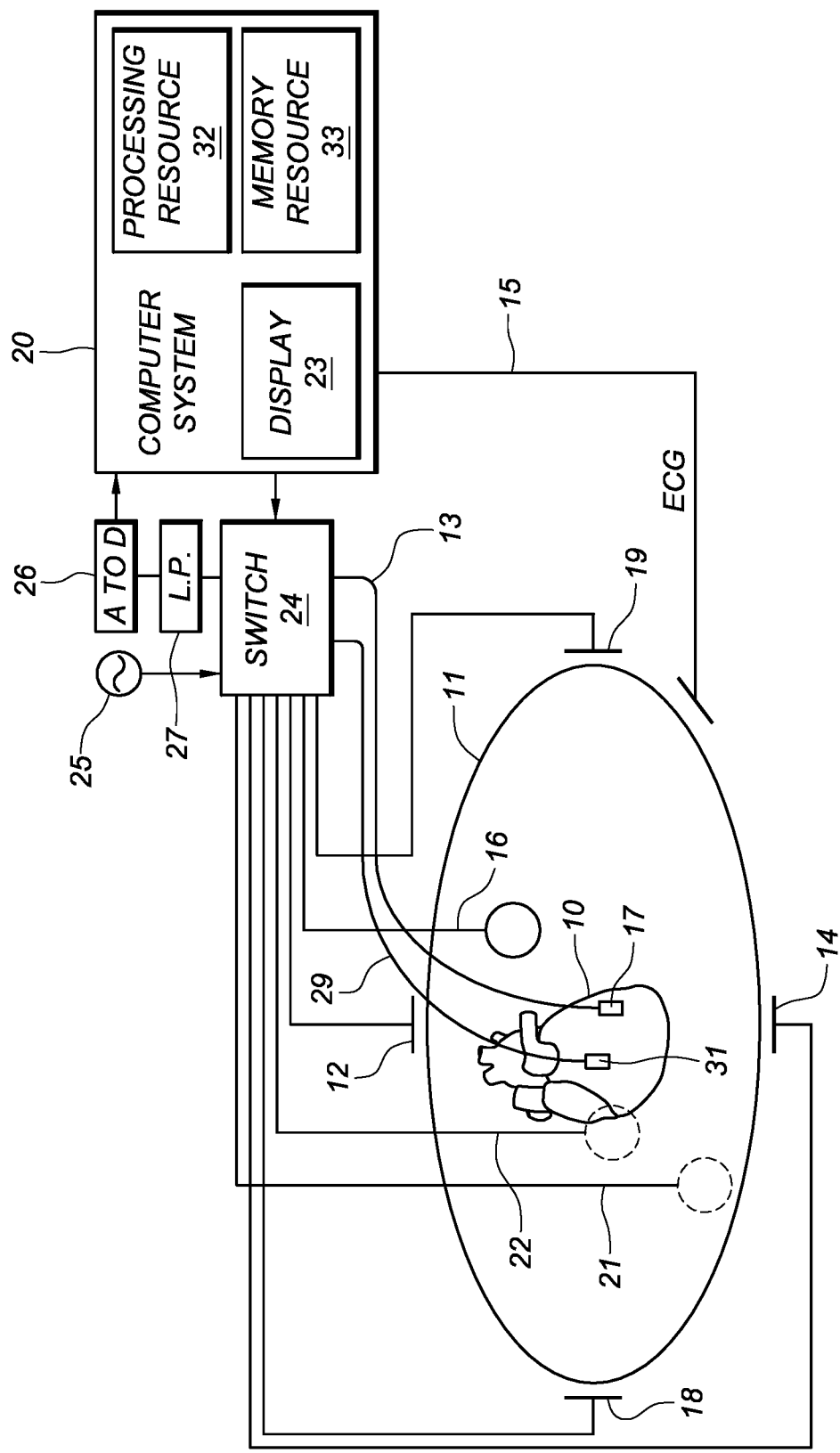
FIG. 1 is a diagrammatic view of an exemplary system for performing one or more diagnostic or therapeutic procedures, in accordance with embodiments of the present disclosure.

Referring now to the drawings wherein like reference numerals are used to identify identical components in the various views, FIG. 1 is a diagrammatic overview of a catheter system in which the invention may be practiced. The system may comprise various visualization, mapping and navigation components as known in the art, including among others, for example, an EnSite™ Velocity™ Cardiac Mapping and Visualization System commercially available from Abbott Laboratories, as further discussed herein.

The system may be used in connection with or for various medical procedures, for example, mapping of the heart and/or cardiac ablation procedures. In one embodiment, the medical positioning system 14 may comprise a magnetic field-based system such as, for example, the CARTO™ System available from Biosense Webster, and as generally shown with reference to one or more of U.S. Pat. Nos. 6,498,944; 6,788,967; and 6,690,963, the entire disclosures of which are incorporated in their entireties as though fully set forth herein. In another embodiment, the magnetic field based system can partly comprise a magnetic field based system such as the MediGuide™ Technology system from Abbott Laboratories, and as generally shown with reference to one or more of U.S. Pat. Nos. 6,233,476; 7,197,354; and 7,386,339; U.S. patent application Ser. No. 14/208,120 entitled "Medical Device Navigation System" filed on 13 Mar. 2014, U.S. Provisional Patent Application No. 61/834,223 entitled "Medical Device Navigation System" filed on 12 Jun. 2013, and International Application No. PCT/IB2014/059709 entitled "Medical Device Navigation System" filed on 13 Mar. 2014, the disclosures of which are hereby incorporated by reference in their entireties as though fully set forth herein. In yet another embodiment, the medical positioning system 14 may comprise a combination magnetic field-based system and electric field-based system such as, for example and without limitation, the systems described in pending U.S. patent application Ser. No. 13/231,284 entitled "Catheter Navigation Using Impedance and Magnetic Field Measurements" filed on 13 Sep. 2011 and U.S. patent application Ser. No. 13/087,203 entitled "System and Method for Registration of Multiple Navigation Systems to a Common Coordinate Frame" filed on 14 Apr. 2011, each of which is hereby incorporated by reference in its entirety as though set fully forth herein, or the CARTO™ 3 system commercially available from Biosense Webster. In some embodiments, the medical positioning system 14 can comprise or be used in conjunction with other commonly available systems, such as, for example and without limitation, fluoroscopic, computed tomography (CT), and magnetic resonance imaging (MRI)-based systems. For purposes of clarity and illustration only, the medical positioning system 14 will be described hereinafter as comprising a hybrid magnetic and impedance tracking system. Although reference is made to cardiac mapping of the heart, one or more aspects of the present disclosure may apply to other anatomic structures.

With reference to FIG. 1, the catheter system includes a diagrammatic depiction of a heart 10 of a patient 11. The system includes the ability to receive a plurality of catheter locations as the catheter distal end is swept around and within a chamber of the heart. For this purpose, FIG. 1 shows an exemplary catheter localization system of the type based on externally-applied orthogonal electric fields which are used to determine the location of one or more catheter position sensors. Such a system can include an impedance localization system and/or hybrid magnetic and impedance tracking system such an EnSite™ NavX™ Electro Anatomical Mapping System, an EnSite™ Velocity™ Electro Anatomical Mapping System, and an EnSite Precision™ Electro Anatomical Mapping System, all commercially available from Abbott Laboratories, or as seen generally by reference to U.S. Pat. No. 7,263,397 (the '397 patent), or U.S. Patent Publication No. 2007/0060833 A1, U.S. application Ser. No. 11/227,580 filed 15 Sep. 2005 (the '580 application), or US Publication No. 2018/0296111 A1, U.S. application Ser. No. 15/953,155 filed 13 Apr. 2018 (the '155 application). The '397 patent, the '580 application, and the '155 application are all hereby incorporated by reference as though fully set forth herein. The various EnSite™ systems are based on the principal that when electrical currents are passed through the thorax, a voltage drop occurs across internal organs such as the heart and this voltage drop can be measured and used to determine the position of a medical device within the body. It should be understood, however, that this embodiment is exemplary only and not limiting in nature. Other technologies for determining the location in 3D space of a catheter, such as the MediGuide™ system, may be used in practicing the present invention, including for example, the CARTO™ navigation and location system of Biosense Webster, Inc., or the AURORA® system of Northern Digital Inc., both of which utilize magnetic fields rather than electrical fields. Accordingly, as used herein, a sensor is provided for producing signals indicative of catheter location information, and may include one or more position sensors. The position sensors can include one or more electrodes configured to detect one or more characteristics of an electrical field, for example in the case of an impedance-based localization system, or alternatively, one or more coils (e.g., wire windings) configured to detect one or more characteristics of a magnetic field, for example, in the case of a magnetic-field based localization system.

It should be further understood that in some localization systems, one or more position sensors may collectively define the sensor. The one or more position sensors may be provided on a distal end of a catheter and the localization system may be configured to obtain location information from the one or more position sensors. The localization system may compute a distal location of the catheter using not only the received location information, but also a geometrical relationship between the one or more position sensors providing the location information and the distal location on the catheter (e.g., one piece of geometrical information may be the ring electrode to tip distance). Finally, the localization system may use the computed location, as if it were collected directly. Likewise, in a magnetic field based localization embodiment, the catheter tip and the magnetic coil may have a geometrical relationship therebetween where the localization system is configured to use the computed tip location (i.e., computed based on the magnetic coil signals and predefined knowledge of the geometrical relationship between coil and tip) as if such location were collected directly. Of course, other variations are possible.

With continued reference to FIG. 1, in the illustrated impedance-based localization system embodiment, three sets of surface electrodes (e.g., applied via a patch) are shown: X-axis electrodes 12, 14; Y-axis electrodes 18, 19; and Z-axis electrodes 16, 22. In some embodiments, an additional surface electrode 21 (e.g., applied via a "belly" patch) may be used. The surface electrodes are all connected to a switch 24. A representative catheter 13 is shown, which has a single distal electrode 17, which may be referred to herein as a "roving" or "measurement" electrode. In some embodiments, the catheter 13 can be a coronary sinus catheter or a right ventricle apex catheter. The electrode 17 may define the position sensor in this embodiment, but as alluded to above, many variations are possible and the catheter 13 can include multiple position sensors, as discussed further herein. FIG. 1 also shows a second, independent catheter 29 with a fixed reference electrode 31, which may be stationary on the heart 10 for calibration purposes.

FIG. 1 further shows a computer system 20, a signal generator 25, an analog-to-digital converter 26 and a low-pass filter 27. The computer system 20 can utilize software, hardware, firmware, and/or logic to perform a number of functions described herein. The computing system 20 can be a combination of hardware and instructions to share information. The hardware, for example can include processing resource 32 and/or a memory resource 33 (e.g., non-transitory computer-readable medium (CRM) database, etc.). A processing resource 32, as used herein, can include a number of processors capable of executing instructions stored by the memory resource 33. The processing resource 32 can be integrated in a single device or distributed across multiple devices. The instructions (e.g., computer-readable instructions (CRI)) can include instructions stored on the memory resource 33 and executable by the processing resource 32 for aligning a cardiac model.

The computer system 20 is configured to control the signal generator 25 in accordance with predetermined strategies to selectively energize various pairs of surface electrodes. In operation, the computer system 20 is configured to obtain raw patch data (i.e., voltage readings) via the filter 27 and A-D converter 26 and use this raw patch data to determine the raw electrode location coordinates in three-dimensional space (X, Y, Z) of a catheter electrode positioned inside the heart 10 or chamber thereof (e.g., such as the roving electrode 17 mentioned above). In some embodiments, a phase of the patient's 11 cardiac cycle can be measured or otherwise determined when such electrode location coordinates are being received. For this purpose, in an embodiment, most or all of the conventional twelve (12) ECG leads, coupled to body surface electrodes and designated collectively by reference numeral 15, are provided to support the acquisition of an electrocardiogram (ECG) of the patient 11.

Alternatively, a reference electrode positioned in a fixed location in the heart 10, such as fixed reference electrode 31, may be used to provide a relatively stable signal that can be analyzed to determine the cardiac phase of the heart 10 in the cardiac cycle (e.g., placed at the coronary sinus). More generally, another catheter having an electrode, other than the moving or roving catheter, may be placed and maintained in a constant position relative to the heart 10 to obtain a relatively stable signal indicative of cardiac phase. As shown, the ECG leads 15 are coupled directly to the computer system 20 for acquisition and subsequent processing to obtain the phase of the heart 10 in the cardiac cycle. The ECG leads 15 may also be provided to other systems (not shown).

As previously mentioned, embodiments of the present disclosure can be used with a magnetic field-based system. Some embodiments can include a main electronic control unit (e.g., one or more processors) having various input/output mechanisms, a display 23, an optional image database, a localization system such as a medical positioning system (VIPS) (electromagnetic sensor tracking system), an electrocardiogram (ECG) monitor, one or more MPS location sensors (e.g., patient reference sensor), and an MPS-enabled medical device (such as an elongated catheter or introducer) which itself includes one or more of the above-described MPS location sensors. As discussed, in some embodiments, the medical positioning system may comprise a magnetic field-based system such as, for example, the MediGuide™ Technology system from Abbott Laboratories, and as generally shown with reference to one or more of U.S. Pat. Nos. 6,233,476; 7,197,354; and 7,386,339; U.S. patent application Ser. No. 14/208,120 entitled "Medical Device Navigation System" filed on 13 Mar. 2014, U.S. Provisional Patent Application No. 61/834,223 entitled "Medical Device Navigation System" filed on 12 Jun. 2013, and International Application No. PCT/IB2014/059709 entitled "Medical Device Navigation System" filed on 13 Mar. 2014, the disclosures of which are hereby incorporated by reference in their entireties as though fully set forth herein.

Embodiments can include input/output mechanisms, which can comprise conventional apparatus for interfacing with a computer-based control unit, for example, a keyboard, a mouse, a tablet, a foot pedal, a switch or the like. Embodiments can also include a display 23, which can also comprise conventional apparatus.

Embodiments may find use in navigation applications that use imaging of a region of interest. Therefore, the magnetic field-based system may optionally include an image database. The image database may be configured to store image information relating to the patient's body, for example, a region of interest surrounding a destination site for the medical device and/or multiple regions of interest along a navigation path contemplated to be traversed by the device to reach the destination site. The image data in the image database may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus) wherein the image database acts as a buffer (live fluoroscopy); and/or (3) a sequence of related two-dimensional images defining a cine-loop (CL), wherein each image in the sequence has at least an ECG timing parameter associated therewith adequate to allow playback of the sequence in accordance with acquired real-time ECG signals obtained from the ECG monitor. It should be understood that the foregoing are examples only and not limiting in nature. For example, the image database may also include three-dimensional image data. It should be further understood that the images may be acquired through any imaging modality, now known or hereafter developed, for example X-ray, ultra-sound, computerized tomography, nuclear magnetic resonance or the like.

The MPS can be configured to serve as the localization system and therefore to determine positioning (localization) data with respect to one or more of MPS location sensors, one or more medical devices, and/or on one or more patient reference sensors (PRS), and output a respective location reading. The location readings may each include at least one or both of a position and an orientation (P&O) relative to a reference coordinate system, which may be the coordinate system of the MPS. For example, the P&O may be expressed as a position (i.e., a coordinate in three axes X, Y, and Z) and orientation (i.e., an azimuth and elevation) of a magnetic field sensor in a magnetic field relative to a magnetic field generator(s) or transmitter(s).

The MPS determines respective locations (i.e., P&O) in the reference coordinate system based on capturing and processing signals received from the magnetic field sensors, while such sensors are disposed in a controlled low-strength AC magnetic field. From an electromagnetic perspective, these sensors develop a voltage that is induced on the coil residing in a changing magnetic field, as contemplated here. The sensors are thus configured to detect one or more characteristics of the magnetic field(s) in which they are disposed and to generate an indicative signal, which is further processed by the MPS to obtain a respective P&O of the sensors. Exemplary design features and manufacturing processes and methods for the sensors and medical devices incorporating such sensors may be found in U.S. Pat. No. 8,636,718, the entirety of which is incorporated by reference herein.

The MPS sensor, and optionally additional MPS sensors in further embodiments, may be associated with the MPS-enabled medical device. Another MPS sensor, namely, a patient reference sensor (PRS) is configured to provide a positional reference of the patient's body so as to allow motion compensation for gross patient body movements and/or respiration-induced movements. The PRS may be attached to the patient's manubrium sternum, a stable place on the chest, or another location that is relatively positionally stable. Like MPS location sensor, the PRS is configured to detect one or more characteristics of the magnetic field in which it is disposed, wherein the MPS provides a location reading (e.g., a P&O reading) indicative of the PRS's position and orientation in the reference coordinate system.

The electro-cardiogram (ECG) monitor is configured to continuously detect an electrical timing signal of the heart organ through the use of a plurality of ECG electrodes (not shown), which may be externally-affixed to the outside of a patient's body. The timing signal generally corresponds to the particular phase of the cardiac cycle, among other things. Generally, the ECG signal(s) may be used by the control unit for ECG synchronized playback of a previously captured sequence of images (cine loop) stored in the database. The ECG monitor and the ECG-electrodes may both comprise conventional components.

The magnetic field-based system can be incorporated into or associated with a fluoroscopic imaging system, which may include commercially available fluoroscopic imaging components, for example, an x-ray source, a C-Arm, and/or an x-ray image intensifier or detector (i.e., "Catheter Lab"). The MPS (electromagnetic sensor tracking system) includes a magnetic transmitter assembly (MTA) (electromagnetic field generator) and a magnetic processing core for determining location (P&O) readings. The MTA is configured to generate the magnetic field(s) in and around the patient's chest cavity, in a predefined three-dimensional space identified as a motion box.

The MPS sensors are, as described above, configured to sense one or more characteristics of the magnetic field(s) when the sensors are in a motion box, and each generate a respective signal that is provided to the magnetic processing core. The processing core is responsive to these detected signals and is configured to calculate respective P&O readings for each MPS sensor in the motion box. The processing core can detect when an MPS sensor exits the motion box. Thus, the MPS enables real-time tracking of each sensor in three-dimensional space.

The actual volume of the motion box may be stored in, for example, the processing core, and processing core is able to determine the positions and orientations of each sensor in relation to the boundaries of motion box. Alternatively, the actual volume of motion box may be stored in, for example, the main control, and the main control may be able to determine the positions and orientations of each sensor in relation to the boundaries of the motion box. Accordingly, the system can evaluate (e.g., in the processing core or in the main control) whether a sensor is within, at the boundary of, or outside of the motion box. Based on this information, the motion box and sensor(s) can be displayed in relation to one another on the display as described in greater detail elsewhere herein.

In some alternative embodiments, the MTA can be located underneath a patient examination table, between an x-ray source and the patient examination table. For example, the MTA can be connected with the patient examination table. In some embodiments, as discussed herein, the MTA can be a mobile device, which can be placed on a chest of the patient and used to generate the magnetic field for tracking of the object.

The positional relationship between the image coordinate system and the MPS reference coordinate system (electromagnetic tracking coordinate system) may be calculated based on a known optical-magnetic calibration of the system (e.g., established during setup), since the positioning system and imaging system may be considered fixed relative to each other in such an embodiment. However, for other embodiments using other imaging modalities, including embodiments where the image data is acquired at an earlier time and then imported from an external source (e.g., imaging data stored in the database), a registration step registering the MPS coordinate system and the image coordinate system may need to be performed so that MPS location readings can be properly coordinated with any particular image being used.

Figure 2A:
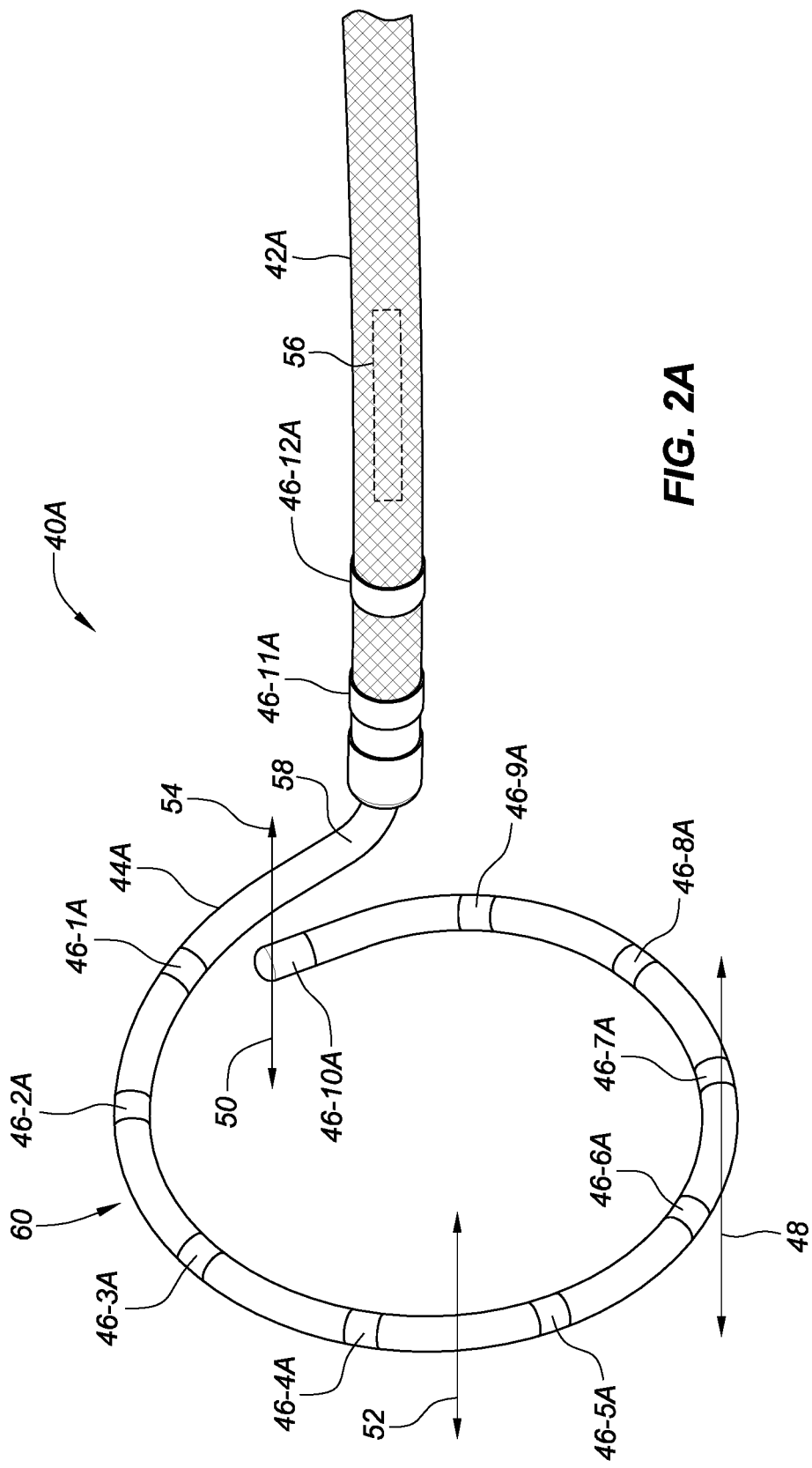
FIG. 2A depicts an isometric side view of an electrophysiology catheter, in accordance with embodiments of the present disclosure.

FIG. 2A depicts an electrophysiology catheter 40A, in accordance with embodiments of the present disclosure. The electrophysiology catheter 40A can be used in an electrophysiology procedure to help doctors understand a nature of abnormal heart rhythms (e.g., arrhythmias) and can include features as further discussed in WO 2017/177121, which is hereby incorporated by reference as though fully set forth herein. The procedure is performed by inserting the electrophysiology catheter 40A, which measures electrical activity, through blood vessels that enter the heart. Each electrophysiology catheter 40A can include several electrodes 46-1A, 46-2A, . . . , 46-12A connected to a computer system (e.g., computer system 20 in FIG. 1) via a connection box. Hereinafter, the electrodes 46-1A, 46-2A, . . . , 46-12A are referred to in the plural as electrodes 46A. The electrodes 46A can be disposed on a flexible tip portion 44A, which can be a circular tip, as depicted. However, the tip can be formed as other shapes, in some embodiments.

The electrophysiology catheter 40A can include a magnetic position sensor 56, in some embodiments, disposed in and/or on the shaft 42A. The electrodes can detect one or more characteristics of an electrical field in which the electrodes 46A are disposed. As previously discussed herein, in relation to FIG. 1, the electrical field can be produced by surface electrodes (e.g., patch electrodes) placed on an exterior of the patient. Based on the impedances associated with signals received from the electrodes 46A, a position (e.g., coordinate(s)) of the electrophysiology catheter 40A can be determined. In some embodiments, the electrophysiology catheter 40A can be an Advisor™ FL Circular Mapping Catheter, Sensor Enabled™, as produced by Abbott Laboratories, although the electrophysiology catheter 40A can be another type of electrophysiology catheter, in some embodiments. The catheter 40A can be used in conjunction with an EnSite™ Velocity™ Electro Anatomical Mapping System, an EnSite Precision™ Electro Anatomical Mapping System, and/or a MediGuide™ system, among other types of systems, for example those mentioned herein.

Figure 2B:
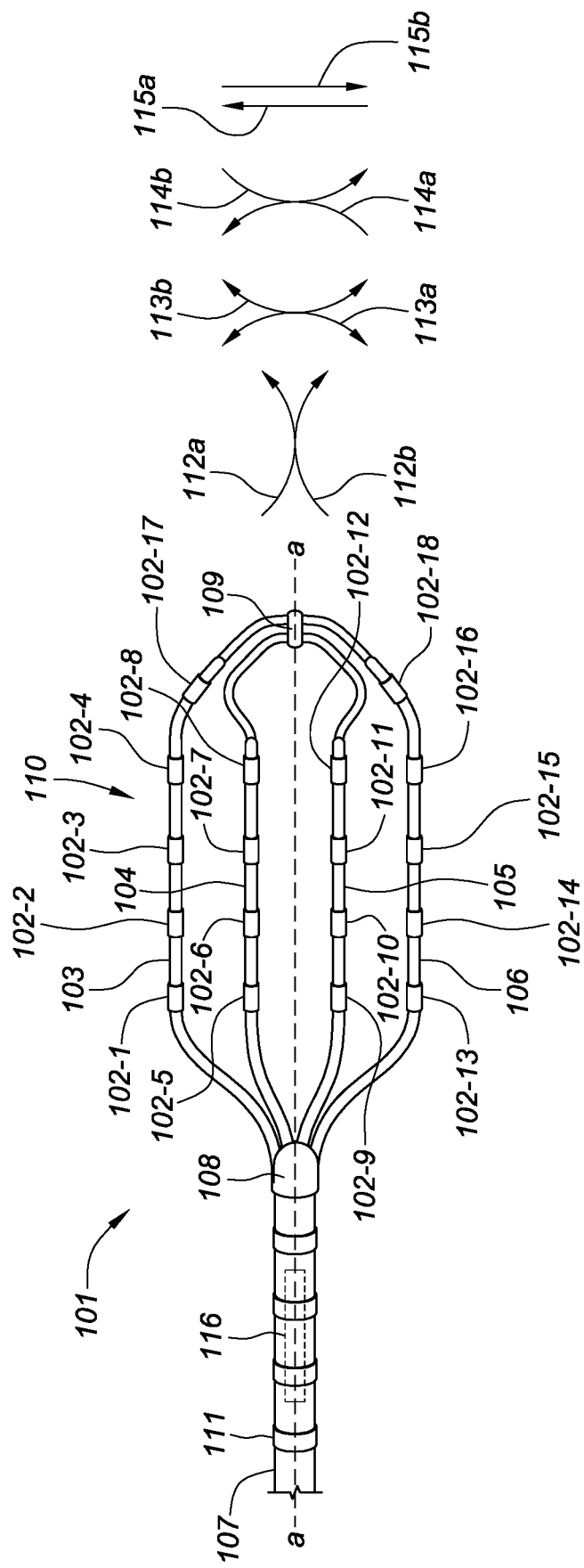
FIG. 2B depicts a top view of a second type of electrophysiology catheter, in accordance with embodiments of the present disclosure.

FIG. 2B is a top view of a second type of electrophysiology catheter 101, in accordance with embodiments of the present disclosure. The electrophysiology catheter is also referred to herein as a high-density electrode catheter 101. In some embodiments, the high-density electrode catheter 101 can include a flexible tip portion 110 that forms a flexible array of electrodes 102. This planar array (or 'paddle' configuration) of electrodes 102 comprises four side-by-side, longitudinally-extending arms 103, 104, 105, 106, which can form a flexible framework on which the electrodes 102 are disposed. The four electrode-carrier arms can comprise a first outboard arm 103, a second outboard arm 106, a first inboard arm 104, and a second inboard arm 105, which can be joined at a distal end by a distal connective portion 109, although not required. These arms can be laterally separated from each other.

Each of the four arms can carry a plurality of electrodes 102. For example, each of the four arms can carry electrodes 102 spaced along a length of each of the four arms. Although the high-density electrode catheter 101 depicted in FIG. 2B depicts four arms, the high-density electrode catheter 101 could comprise more or fewer arms. Additionally, while the high-density electrode catheter 101 depicted in FIG. 2B depicts 18 electrodes (e.g., 5 electrodes on the first outboard arm 103 and second outboard arm 106 and 4 electrodes on the first inboard arm 104 and second inboard arm 105), the catheter can include more or fewer than 18 electrodes. In addition, the first outboard arm 103 and second outboard arm 106 can include more or fewer than 5 electrodes and the first inboard arm 104 and second inboard arm 105 can include more or fewer than 4 electrodes).

In some embodiments, the electrodes 102 can be used in diagnostic, therapeutic, and/or mapping procedures. For example and without limitation, the electrodes 102 can be used for electrophysiological studies, pacing, cardiac mapping, and ablation. In some embodiments, the electrodes 102 can be used to perform unipolar or bipolar ablation. This unipolar or bipolar ablation can create specific lines or patterns of lesions. In some embodiments, the electrodes 102 can receive electrical signals from the heart, which can be used for electrophysiological studies. In some embodiments, the electrodes 102 can perform a location or position sensing function related to cardiac mapping.

In some embodiments, the high-density electrode catheter 101 can include a catheter shaft 107. The catheter shaft 107 can include a proximal end and a distal end. The distal end can include a connector 108, which can couple the distal end of the catheter shaft 107 to a proximal end of the planar array. The catheter shaft 107 can define a catheter shaft longitudinal axis a-a, as depicted in FIG. 1A, along which the first outboard arm 103, first inboard arm 104, second inboard arm 105, and second outboard arm 106 can generally extend parallel in relation therewith. The catheter shaft 107 can be made of a flexible material, such that it can be threaded through a tortuous vasculature of a patient. In some embodiments, the catheter shaft 107 can include one or more ring electrodes 111 disposed along a length of the catheter shaft 107 and one or more magnetic position sensors 116 located in or along the shaft 107. The ring electrodes 111 can be used for diagnostic, therapeutic, and/or mapping procedures, in an example.

Embodiments of the present disclosure can generate a visual representation of a catheter. As discussed above, a catheter can have a catheter shaft and a flexible tip portion that includes a plurality of electrodes. The flexible tip portion can generally be flexible enough to conform to a tissue of a patient, allowing for some or all of the plurality of electrodes disposed on the flexible tip portion to contact the tissue of the patient. The flexible nature of the tip portion, however, can prove to be problematic when trying to determine a visual representation of the flexible tip portion, and the catheter in general. The electrodes on the flexible tip portion can be subject to shift and/or drift in an impedance field generated by one or more electrode patches that are in contact with the patient's body, which can result in deviations of calculated impedance based locations versus an actual location of the electrode. Various methods have been used to calculate positions of the plurality of electrodes disposed on the flexible tip portions, especially the impedance transform, which provides a relation between impedance positions and real world positions. However, this transform is not simple to find and is time and position dependent.

Embodiments of the present disclosure can determine a visual representation of the flexible tip portion and the catheter as a whole by using raw impedance positions derived from the electric field inside the heart by using angles between the raw impedance positions and applying properties of the electrical field in which the electrodes disposed on the flexible tip portion of the catheter are disposed.

FIG. 3 depicts a method 120 for determining a shape of a catheter, in accordance with embodiments of the present disclosure. In some embodiments, the method can include receiving 122 a plurality of impedance measurements from a plurality of electrodes disposed on a flexible tip portion of the catheter. As discussed in relation to FIGS. 2A and 2B, a plurality of impedance measurements can be received from the electrodes 46-1A, 46-2A, . . . , 46-10A disposed on the catheter 40A depicted in FIG. 2A and/or a plurality of impedance measurements can be received from the electrodes 102-1, 102-2, . . . , 102-18, disposed on the flexible tip portion 110 of the high-density electrode catheter 101 in FIG. 2B.

The method can include receiving 124 a magnetic position measurement from a magnetic position sensor disposed on a shaft of the catheter. For example, the catheter shaft 42A (FIG. 2A) can include a magnetic position sensor 56 and the catheter shaft 107 (FIG. 2B) can also include a magnetic position sensor 116, from which a magnetic position measurement can be received.

The method 120 can include determining 126 a relationship between each of the plurality of electrodes disposed on the flexible tip portion of the catheter based on the impedance measurements received from the plurality of electrodes. In some embodiments, determining the relationship between each of the plurality of electrodes disposed on the flexible tip portion of the catheter can include determining an angle between each of the plurality of electrodes. In an example, an angle can be determined between any number of electrodes disposed on the flexible tip portion of the catheter. In some embodiments, an angle can be determined between at least three electrodes disposed on the flexible tip portion of the catheter. In some embodiments, three electrodes can be a minimum number of electrodes used for determining an angle between the electrodes. In some embodiments, the angle can be determined using several pairs of electrodes to measure a bending, yaw, twist, etc. of the flexible tip portion of the catheter using the several pairs of electrodes.

In some embodiments, the impedance measurements used in determining the angle between each of the plurality of electrodes disposed on the flexible tip portion of the catheter can be raw impedance measurements. In some embodiments, using the raw impedance can allow for fewer computations to be performed when determining the angles between the electrodes. As a result of using the raw impedance, the positions of the electrodes 46A, 102 can be shifted with respect to their actual location. However, the positions of each electrode 46A, 102 can be assumed to have shifted by approximately the same amount, making it possible to determine a general shape of the flexible tip portion, even if it has experienced shift and/or drift. In some embodiments, prior to determining the angles between the electrodes, the raw impedance measurements can be transformed from an impedance domain to a magnetic domain through use of local field scaling, as further discussed herein.

The field in which the electrodes 46A, 102 are disposed can be considered an electrostatic field, which can be described by the Poisson's formula when no change of charge occurs inside, using the Laplace equation. Furthermore, an assumption can be made that no magnetic field is acting upon the volume in which the electrodes 46A, 102 are disposed. Thus, no curl may exist in the electrostatic field, since magnetic fields can act as vortices upon electrical currents. In some embodiments, a size (e.g., longitudinal length and/or lateral width) of the flexible tip portion of the catheters 40A, 101 can be approximately 2 centimeters. However the size can be greater or smaller than 2 centimeters, in some embodiments. Because of the relatively small size of the flexible tip portion of the catheter 40A, 101, properties of the electrostatic field can remain relatively uniform throughout the space in which the flexible tip portion of the catheter is disposed. For example, with reference to FIG. 4, which is a graphical depiction 140 of electrostatic field lines 142 in relation to a particular domain 144, minimal curl is present within the domain. In some embodiments, because of the relatively small size of the flexible tip portion of the catheter, a local field scaling can be assumed constant over the flexible tip portion. For example, as discussed further herein, impedance measurements received from the electrodes 46A, 102 can be transformed from an impedance domain to a magnetic domain through use of local field scaling. An assumption can be made that the scaling is constant over the relatively small size of the flexible tip portion of the catheter.

Figure 4:
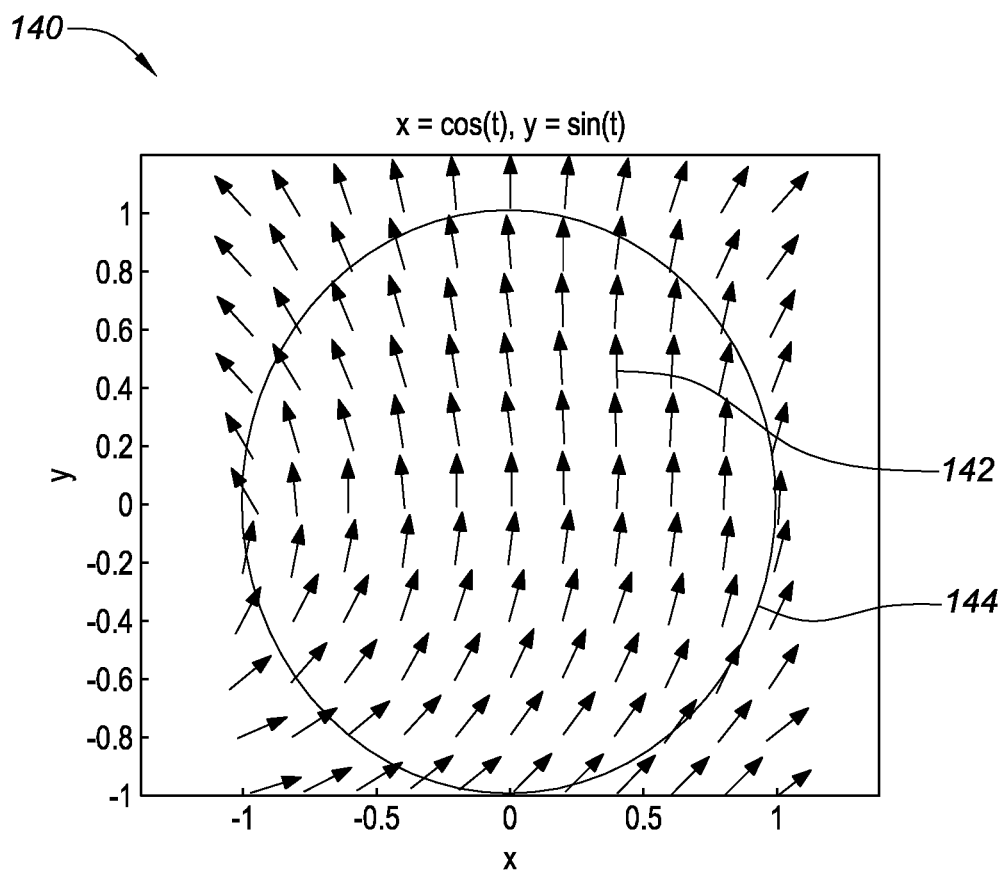
FIG. 4 depicts a graphical depiction of electrostatic field lines in relation to a particular domain, in accordance with embodiments of the present disclosure.

As depicted in FIG. 4, the x-axis and y-axis represent a distance, which in this case is represented in centimeters. The domain 144 is approximately the size of the flexible tip portions 44A, 110, depicted in FIGS. 2A and 2B. As seen in FIG. 4, a minimal change in direction of the electrostatic field is present within the relatively small domain 144, which is depicted as approximately two centimeters by two centimeters, although the domain can be larger or smaller depending on a size of the flexible tip portion. Accordingly, even though the data received from the electrodes 46A, 102 disposed on the flexible tip portions 44A, 110 is raw impedance data, angles between each one of the electrodes 46A, 102 can be determined accurately.

In some embodiments, a curl within the electrostatic field inside of the domain 144 can be assumed to be zero in the absence of magnetic fields acting upon the domain 144, which can help reduce the complexity of determining the angles between each of the plurality of electrodes. For example, the directional changes in the electrostatic field, represented by arrows 142, are gradual within the measured domain 144, with respect to the catheters that are used. For example, no bends, loops, twists or other types of variations are present within the electrostatic field potential lines, which are emitted electrostatic field sources and converge at electrostatic field sinks. With conversion of impedance to position based upon ohm's law, total impedance measured is a function of length of path and impedance per unit length, which keeps the above assumptions with respect to minimal directional changes of the electrostatic field within the measured domain 144.

Because of the minimal directional changes of the electrostatic field, angles can be determined between any combination of electrodes 46A, 102, depicted in FIGS. 2A and 2B, to determine a bend, yaw, curvature, and twist, which are further discussed herein in relation to FIGS. 6A to 6D and FIGS. 8A to 8D of the flexible tip portions 44A, 110 of the catheters 40A, 101. With reference to FIG. 2A, the flexible tip portion 44A can experience bending in either direction of arrow 48. For example, with reference to the drawing sheet on which FIG. 2A is presented, the flexible tip portion 44A, where the line 48 intersects, can bend left or right with respect to the page, along either direction of arrow 48. The flexible tip portion 110 can experience bending out of plane, where the flexible tip portion 44A moves in a direction of arrow 50, causing the helix to be formed about the curvature of the loop of the catheter. For example, with reference to the drawings sheet on which FIG. 2A is presented, the flexible tip portion 44A through which the arrow 50 passes can be moved left along the page, causing a helix to be formed in the flexible tip portion 44A. The flexible tip portion 44A can experience twisting, in a direction of arrow 52, as the portion of the flexible tip portion 44A through which the arrow 52 passes is moved in either direction of the arrow 52. The flexible tip portion 110 can experience bending in plane, where the flexible tip portion 44A moves in a direction of arrow 54, causing an in plane curvature of the loop of the catheter. For example, with reference to the drawings sheet on which FIG. 2A is presented, the flexible tip portion 44A through which the arrow 54 passes can be moved right along the page, causing the flexible tip portion 44A of the catheter to be curved in plane.

With reference to FIG. 2B, the flexible tip portion 110 can experience bending in either direction of arrows 112a, 112b. For example, with reference to the drawing sheet on which FIG. 2B is presented, the flexible tip portion 110 can bend into (e.g., in a direction of arrow 112a) or out of (e.g., in a direction of arrow 112b) the page. The flexible tip portion 110 can experience curving, where the flexible tip portion 110 curves about the longitudinal axis a-a. For example, with reference to the drawings sheet on which FIG. 2B is presented, the flexible tip portion 110 can curve into (e.g., in a direction of arrow 113a) or out of (e.g., in a direction of 113b) the page. The flexible tip portion 110 can experience twisting, in a direction of arrow 114a or 114b, where the flexible tip portion 110 is twisted about the longitudinal axis in a first direction (e.g., arrow 114a) or in a second direction (e.g., arrow 114b). The flexible tip portion 110 can experience yaw, in a direction of the arrows 115a or 115b. With reference to the drawing sheet on which FIG. 2B is presented, the flexible tip portion 110 can bend up or down with respect to the page, in a first direction of arrow 115a or in a second direction of arrow 115b.

In some embodiments, the use of raw impedance data from the electrodes when determining the angles between the electrodes can result in data that is noisy. For example, positions of the electrodes determined using the raw impedance data can sometimes be inconsistent, resulting in the appearance that positions of the electrodes have jumped with respect to other electrode positions. Accordingly, the methods of the present disclosure can include filtering the raw impedance measurements received from the plurality of electrodes disposed on the flexible tip portion of the catheter. If the raw impedance data is not filtered, in some embodiments, an incorrect shape of the flexible tip portion of the catheter can be determined. In some embodiments, filtering the raw impedance measurements received from the plurality of electrodes can include filtering the raw impedance measurements with a low pass filter. In some embodiments, prior to filtering, the raw impedance data can be transformed from an impedance domain to a magnetic domain through use of local field scaling, as further discussed herein.

With further reference to FIG. 3, in some embodiments, the method 122 can include predicting 128 a shape of the flexible tip portion of the catheter, based on the determined relationship between each of the plurality of electrodes disposed on the flexible tip portion of the catheter. In some embodiments, the method can include predicting locations of each of the plurality of electrodes disposed on the flexible tip portion 44A, 110 of the catheter. For example, based on the bend, yaw, curvature, and twist that the flexible tip portion 44A, 110 of the catheter is experiencing, an angle between the electrodes 46A, 102 disposed on the flexible tip portion can vary. As discussed above, to determine a change in angle between the electrodes, it can be helpful to have raw impedance data from at least three electrodes, since it can be difficult to determine an angular trend between only two electrodes. Based on the varying angles between the electrodes, a determination of the shape of the flexible portion of the catheter can be determined.

In some embodiments, the method 122 can include predicting the shape of the flexible tip portion of the catheter by calculating the shape using the angle between each of the plurality of electrodes in relation to a shape model of the flexible tip portion. The shape model of the flexible tip portion can factor in bending, yaw, curvature, and/or twist, as discussed above. Embodiments of the present disclosure can include the prediction of a shape model for the flexible tip portion of a catheter, as further discussed herein.

Figure 5:
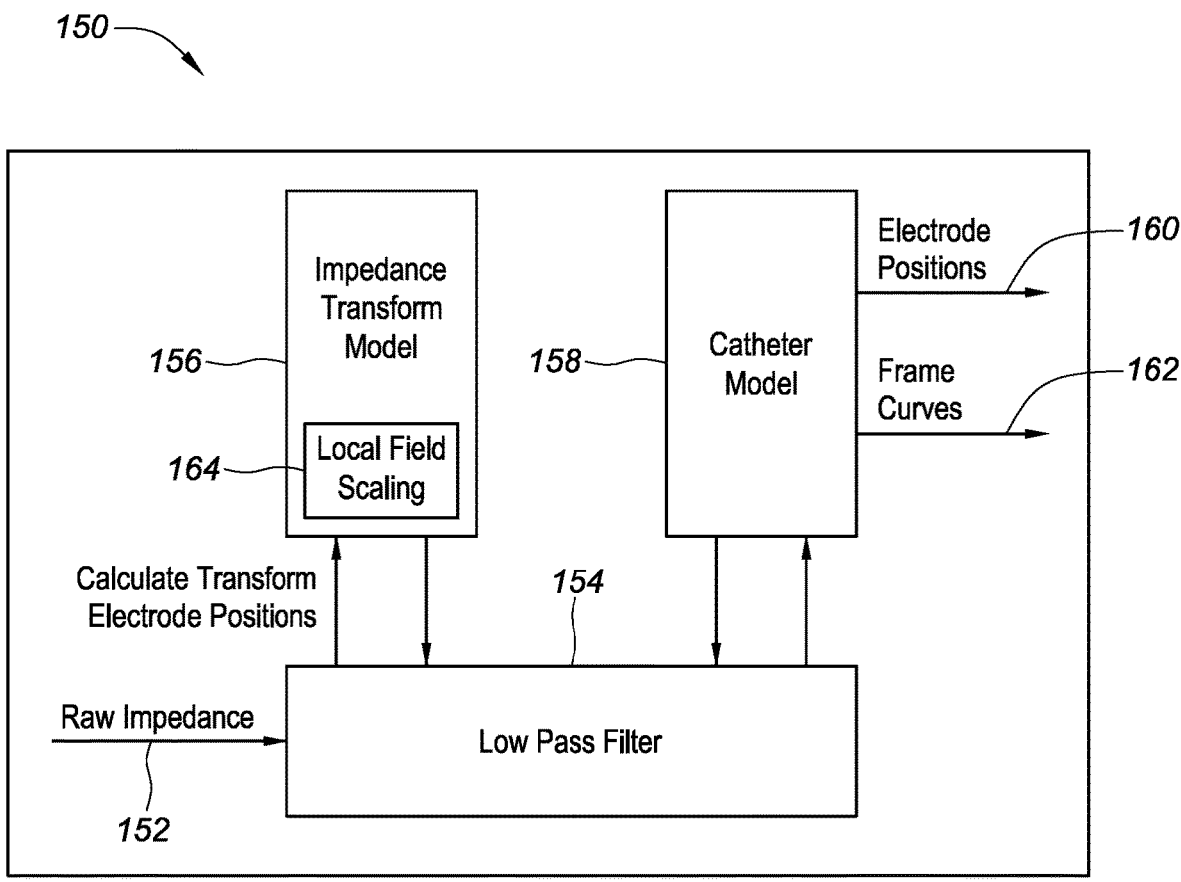
FIG. 5 depicts a system for predicting a shape of a catheter, in accordance with embodiments of the present disclosure.

FIG. 5 depicts a system for predicting a shape of a catheter, in accordance with embodiments of the present disclosure. In some embodiments, raw impedance data can be received, from which electrode positions and frame curves can be calculated. In an example, the raw impedance data can be received from one or more electrodes, as represented by the arrow 152 leading into box 154. In some embodiments, as discussed, a low pass filter 154 can be applied to the raw impedance data 152, at box 154. In some embodiments, electrode positions can be transformed into magnetic space, at box 156. For example, the filtered raw impedance data can be transformed into magnetic data via the impedance transform model, at box 156.

In some embodiments, the impedance transform model can include transforming the raw impedance measurements from an impedance domain to a magnetic domain through use of local field scaling 164. The local field scaling 164 can utilize a rigid body transformation, which can include one or more equations that model a distance between one or more electrode pairs. The constraints of the rigid body transformation can include known distances between the electrodes on the flexible tip portion of the catheter. In an example, a rigid transformation of points from the impedance domain to the magnetic domain can be performed by using the rigid body transformation with the constraints being the known distances between electrodes along the splines or a circular loop of the flexible tip portion of the catheter. However, distances between electrodes on any type of shaped flexible tip portion can be used. For example, embodiments of the present disclosure are not limited to catheters with flexible tip portions such as those depicted and discussed in relation to FIGS. 2A and 2B. In an example, local field scaling 164 associated with the raw impedance measurements can be determined and the raw impedance measurements can be transformed into magnetic positions by scaling the raw impedance measurements based on the local field scaling 164. Once local scaling is completed, raw impedance measurements can be adjusted to rough magnetic positions by scaling them along the x, y, and z axes. To account for discrepancies in the data, the measurements can be filtered (e.g., via a low pass filter 154), as discussed herein.

Some embodiments of the present disclosure include determining a catheter shape model 158, which is further discussed below. As discussed above, the angle between each of the plurality of electrodes can be used in relation to the catheter shape model 158 to calculate the shape of the flexible tip portion of the catheter. The shape model 158 can be used to calculate both electrode positions 160 and frame curves 162. In an example, the electrode positions can be determined from the determined shape of the flexible tip portion. In some embodiments, the electrode positions can be combined and displayed with the frame curves, which have been generated by the catheter model. In some embodiments, the catheter model includes a shape model of the flexible tip portion, which is determined, as further discussed herein.

With further reference to FIG. 3, the method 120 can include determining 130 a shape of the catheter, based on the magnetic position measurement and the predicted shape of the flexible tip portion. For example, with respect to FIGS. 2A and 2B, the magnetic position measurement can be obtained from magnetic position sensors 56, 116. In some embodiments the positional relationship between the catheter shafts 42A, 107 with respect to the flexible tip portions 44A, 110 can be known. The electrode positions can be determined from the raw impedance data; accordingly, the data can be subject to shift and drift. The determined locations of the electrodes, which in some embodiments can be transformed into magnetic positional data, can be shifted such that the determined locations of the electrodes are properly aligned with the position of the magnetic position sensor.

For example, in some embodiments, the method 120 can include determining the shape of the catheter using the angle between each of the plurality of electrodes and the magnetic position measurement in relation to a shape model of the flexible tip portion. In some embodiments, a position and orientation measurement can be received from the magnetic position sensor disposed on the catheter and can be used to determine the shape of the catheter using the angle between each of the plurality of electrodes and the magnetic position and orientation measurement.

In some embodiments, determining the shape of the catheter can include shifting the shape of the flexible tip portion of the catheter in relation to the shaft of the catheter, based on the position and orientation measurement received from the magnetic position sensor. In some embodiments, the shape of the flexible tip portion can first be determined using the raw impedance data received from the electrodes in relation to the shape model of the flexible tip portion. The determined shape of the flexible tip portion can then be correctly positioned with a determined position of the catheter shaft. For example, the determined shape of the flexible tip portion can be correctly positioned, based on the position and orientation measurement received from the magnetic position sensor. Accordingly, determining the shape of the catheter, including the flexible tip portion and the catheter shaft can include shifting the determined shape of the flexible tip portion of the catheter in relation to the shaft of the catheter, based on the position and orientation measurement received from the magnetic position sensor.

Determination of the shape model of the flexible tip portion can include determining a different shape model for catheters with different types of flexible tip portions. For example, a first shape model can be determined for the catheter depicted in FIG. 2A, while a different shape model can be determined for the catheter depicted in FIG. 2B, because the two catheters have different flexible tip portions. Shape models can be determined for other types of flexible tip portions in a similar manner.

In the case of a circular mapping catheter, such as that depicted in FIG. 2A (e.g., the Advisor™ VL Mapping Catheter, available from Abbott Laboratories), the catheter can be modeled based upon the physical behavior of the catheter shape. This solution can involve using the mechanical properties of a simple wire spring to formulate a numerical bending model. The circular mapping catheter shape can be divided into 3 main parts, as depicted in FIG. 2A. The three parts can include the shaft 42A, which is rigid, the knee 58, which is pre-bent by 90 degrees, and the loop 60 (also pre bent by a given angle in the plane of the loop). The determined catheter shape model allows for four different motions, which are also depicted and discussed in relation to FIGS. 6A to 6B. The four different motions include bending around a forward axis of the catheter 40A (e.g., bending) starting at the knee 58, in either direction of arrow 48; bending around a side axis of the catheter 40A (e.g., twisting) starting at the knee 58, in either direction of arrow 52; bending in plane (e.g., loop), around a curvature of the loop 60 of the catheter, in a direction of arrow 52; bending out of plane (e.g., helix), around the curvature of the loop of the catheter, in a direction of arrow 50.

For bend and twist of the loop portion of the catheter, the Euler-Bernoulli beam theory can be used, and the section for which it is subjected can be the top of the knee 58 up to first and second quadrants of the loop 60, which extend approximately to the electrode 46-5A. For the loop 60 angle, the Euler-Bernoulli beam theory can be used, and the section for which it can be used is the entire loop 60 from the knee 58 to the distal end, where the electrode 46-10A is located. For the helix angle, the theory of torsion in mechanics can be used, and the section for which it can be used is the entire loop 60 from knee 58 to distal end where the electrode 46-10A is located.

The theory of torsion can be used as follows. In the field of solid mechanics, torsion can be defined as the twisting of an object due to an applied torque. Torsion can be expressed in either the Pascal (Pa), an SI unit for newtons per square meter, or in pounds per square inch (psi) while torque is expressed in newton meters (N·m) or foot-pound force (ft·lbf). In sections perpendicular to the torque axis, the resultant shear stress in this section can be perpendicular to the radius. In non-circular cross-sections, twisting can be accompanied by a distortion called warping, in which transverse sections do not remain plane. For shafts of uniform cross-section that are unrestrained against warping, the torsion can be expressed as:

$$T = \frac{J_T}{r}\tau = \frac{J_T}{\ell}G\varphi$$

where T is the applied torque or moment of torsion in Nm; Tau is the maximum shear stress at the outer surface; $J_T$ is the torsion constant for the section, approximately the second moment of area about the neutral axis; r is the distance between the rotational axis and the farthest point in the section (at the outer surface); $\ell$ is the length of the object the torque is being applied to or over; φ—(phi) is the angle of twist in radians; G—is the shear modulus, also called the modulus of rigidity.

The shear stress at a point within a shaft can be expressed as:

$$\tau_{\varphi_z} = \frac{Tr}{J_T}$$

The angle of twist can be found by using:

$$\varphi = \frac{T\ell}{GJ_T}$$

For a circular cross section, the same formula applies and the moment of inertia can be defined for a circular cross-section as:

$$I_P = \frac{\pi r^4}{2} = \frac{\pi d^4}{32}$$

The above relation can be expressed as:

$$\theta = \frac{T}{GI_P}$$

where $GI_p$ is defined as torsional rigidity. The angle of twist φ can be expressed as $$\varphi = \theta L = \frac{TL}{GI_P}$$

where φ is measured in radians. Torsional flexibility can be expressed as $$f = \frac{L}{GI_P}$$

and torsional stiffness is expressed as $$k = \frac{GI_P}{L}$$

In addition to torsion, the bending around two perpendicular axes can be factored in and these bending induced stresses can be combined using the rule of superposition. The equations describing the bending of the catheter in bend and twist can be derived from the Euler Bernoulli beam element. The Euler-Bernoulli equation describes the relationship between the beam's deflection and the applied load. The following formula describes the bending curve as a result of distributed load q.

$$\frac{d^2}{dx^2}\left(EI\frac{d^2w}{dx^2}\right) = q$$

The curve w(x) describes the deflection of the beam in the z direction at some position x (recall that the beam is modeled as a one-dimensional object). q is a distributed load, in other words a force per unit length (analogous to pressure being a force per area); it may be a function of x, w, or other variables.

In the above equation, E is the elastic modulus and I is the second moment of area of the beam's cross-section. I can be calculated with respect to the axis that passes through the centroid of the cross-section and which is perpendicular to the applied loading, explicitly, for a beam whose axis is oriented along x with a loading along z, the beam's cross-section is in the YZ plane, and the relevant second moment of area is $$I = \iint z^2 dy\, dz,$$

Successive derivatives of the deflection w have important physical meanings: dw/dx is the slope of the beam and M is the bending moment in the beam, $$M = -EI\frac{d^2w}{dx^2}$$

The Euler Bernoulli theorem can be expanded to a large deflection case, and instead of integration of deflection along the x axis of the beam, the slope can be integrated by sections. The moment can be calculated at each section using the distance from the distal end and a perpendicular force acting upon it. The catheter can be modeled as a circular beam with loads at the end and the bending angle can be integrated per segment by superposition of components which are perpendicular to each other. Since the catheter is pre-bent in the knee section and in the loop section, the shape of the catheter can be composed of an undeformed shape (pre-bent) and a deformed shape, which is the result of three bending components. After numeric integration of the catheter shape along its spine, the electrode positions and the positions of catheter wires upon this shape can be calculated, which can be performed by using the Frenet-Serret formulas, as described below.

In differential geometry, the Frenet-Serret formulas describe the kinematic properties of a particle moving along a continuous, differentiable curve in three-dimensional Euclidean space $\mathbb{R}^3$, or the geometric properties of the curve itself irrespective of any motion. More specifically, the formulas describe the derivatives of the so-called tangent, normal, and binormal unit vectors in terms of each other. Vector notation and linear algebra currently used to write these formulas were not yet in use at the time of their discovery.

The tangent, normal, and binormal unit vectors, often called T, N, and B, or collectively the Frenet-Serret frame or TNB frame, together form an orthonormal basis spanning $\mathbb{R}^3$ and are defined as follows. T is a unit vector tangent to a curve, pointing in the direction of motion; N is a normal unit vector, the derivative of T with respect to an arclength parameter of the curve, divided by its length; and B is a binormal unit vector, the cross product of T and N.

The Frenet-Serret formulas are:

$$\frac{dT}{ds} = \kappa N,$$

$$\frac{dN}{ds} = -\kappa T + \tau B,$$

$$\frac{dB}{ds} = -\tau N,$$

where d/ds is the derivative with respect to arclength, K is the curvature, and r is the torsion of the curve. The two scalars K and r effectively define the curvature and torsion of a space curve. The associated collection, T, N, B, κ, and τ, is called the Frenet-Serret apparatus. Curvature measures the failure of a curve to be a straight line, while torsion measures the failure of a curve to be planar.

The tangent, normal, and binormal unit vectors, often called T, N, and B, or collectively the Frenet-Serret frame or TNB frame, together form an orthonormal basis spanning $\mathbb{R}^3$ and are defined as follows. T is a unit vector tangent to a curve, pointing in the direction of motion; N is a normal unit vector, the derivative of T with respect to an arclength parameter of the curve, divided by its length; and B is the binormal unit vector, the cross product of T and N.

The Frenet-Serret formulas are also known as Frenet-Serret theorem, and can be stated more concisely using matrix notation.

$$\begin{bmatrix} T' \\ N' \\ B' \end{bmatrix} = \begin{bmatrix} 0 & \kappa & 0 \\ -\kappa & 0 & \tau \\ 0 & -\tau & 0 \end{bmatrix} \begin{bmatrix} T \\ N \\ B \end{bmatrix}.$$

The matrix is stored per segment along our catheter spine, and is used for extracting positions of electrodes and curves. As similarly discussed above, the Frenet-Serret frame moving along a helix is represented with T being a unit vector tangent to the curve of the helix and pointing in a direction of motion; N being a normal unit vector, the derivative of T with respect to an arclength parameter of the helical curve, divided by its length; and B being a binormal unit vector, the cross product of T and N. This model can then be compared with data from several sources (e.g., synthetic data, water tank data, animal test data). In embodiments of the present disclosure, a match between synthetic data and calculated shape validated the numerical model and showed small errors for all measured positions and electrodes.

Figure 6A:
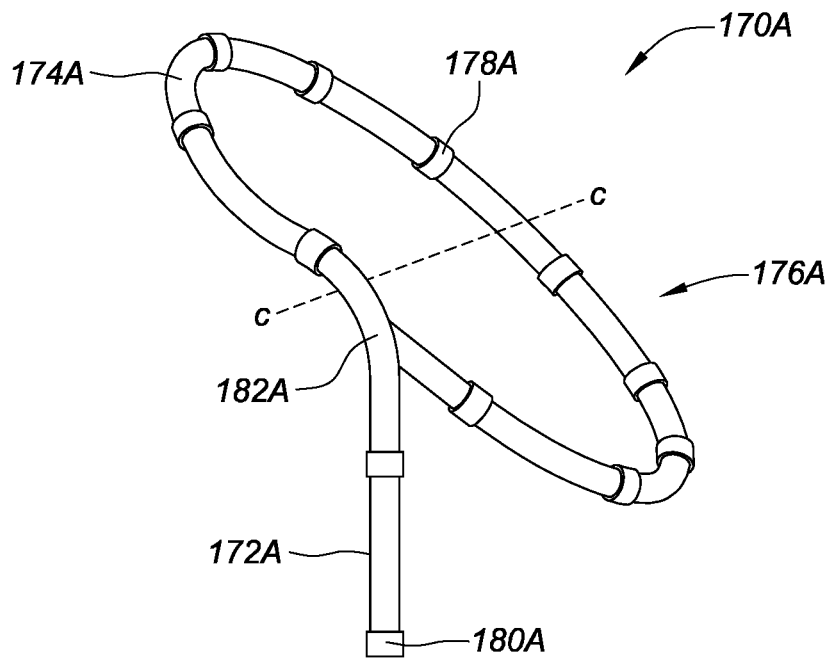
FIGS. 6A to 6D depict parameters used to define the shape of a circular mapping catheter, in accordance with embodiments of the present disclosure.

FIGS. 6A to 6D depict the parameters used to define the shape of the circular mapping catheter, in accordance with embodiments of the present disclosure. As depicted in FIG. 6A, the catheter shape model can account for a bending of the flexible tip portion 176A of the catheter 170A around a forward axis c-c of the catheter 170A, starting at a knee 182A of the catheter 170A. The depicted bending of the flexible tip portion 176A of the catheter 170A is also depicted in relation to arrow 52 of FIG. 2A. As depicted, the catheter 170A includes a catheter shaft 172A connected to a flexible tip portion 176A that is formed from a looped distal end 174A. The looped distal end 178A includes a plurality of electrodes 178A, only one of which is labeled for ease of illustration, and a catheter shaft 172A further includes a plurality of electrodes 180A, only one of which is labeled.

Figure 6B:
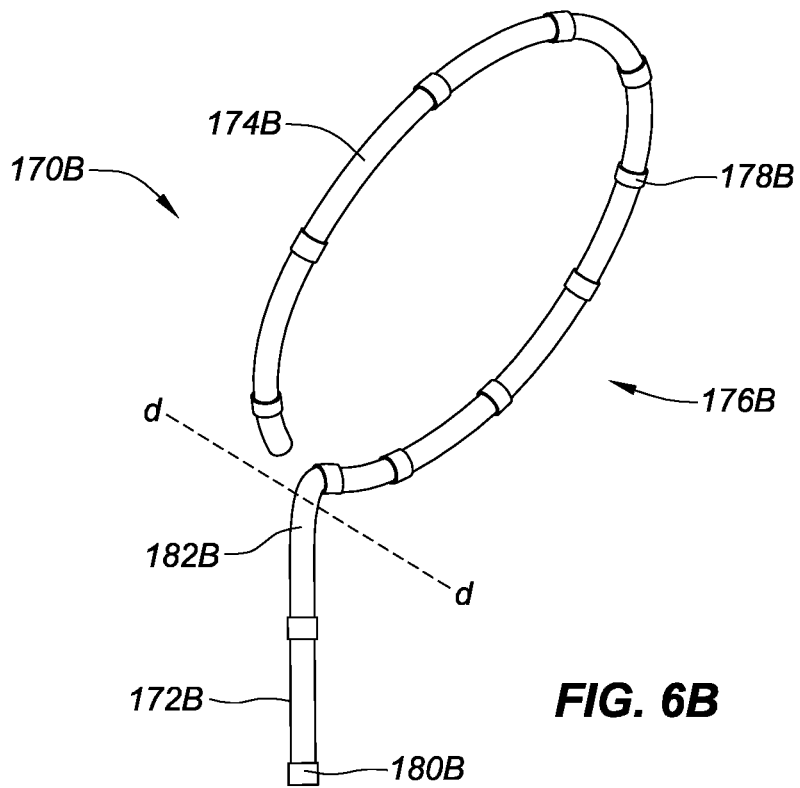

As depicted in FIG. 6B, the catheter shape model can account for a bending of the flexible tip portion 176B of the catheter 170B around a side axis d-d of the catheter 170B, starting at a knee 182B of the catheter 170B. The depicted bending of the flexible tip portion 176B of the catheter 170B is also depicted in relation to arrow 48 of FIG. 2A. As depicted, the catheter 170B includes a catheter shaft 172B connected to a flexible tip portion 176B that is formed from a looped distal end 174B. The looped distal end 178B includes a plurality of electrodes 178B, only one of which is labeled for ease of illustration, and a catheter shaft 172B further includes a plurality of electrodes 180B, only one of which is labeled.

Figure 6C:
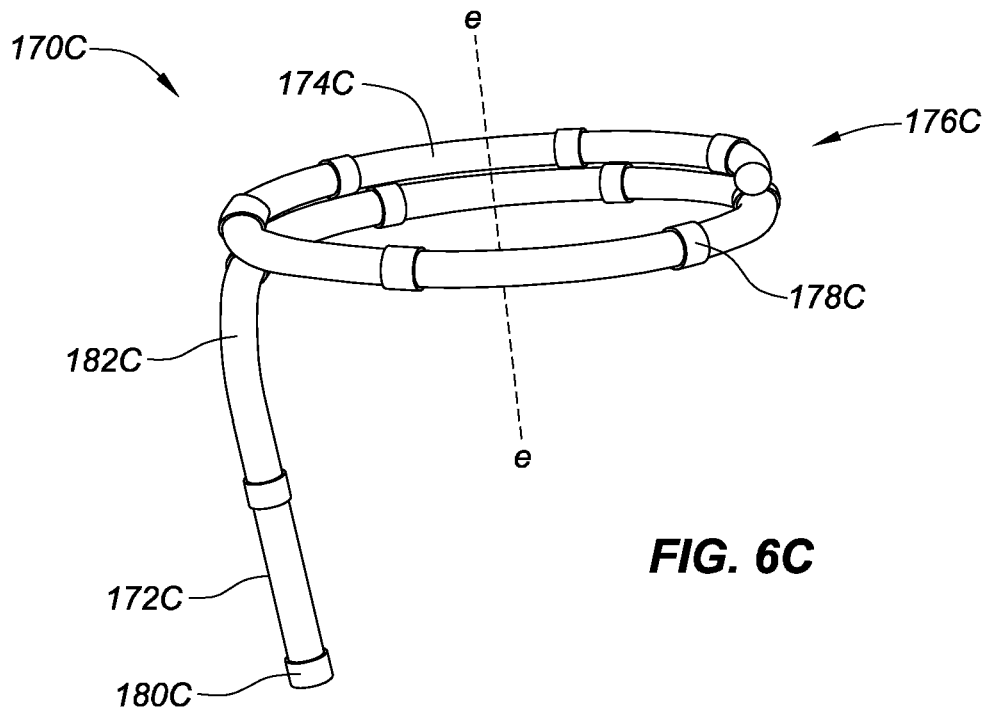

As depicted in FIG. 6C, the catheter shape model can account for a bending of the flexible tip portion 176C of the catheter 170C in plane, around a curvature of the looped distal end 176C of the catheter 170C. The depicted bending of the flexible tip portion 176C of the catheter 170C is also depicted in relation to arrow 54 of FIG. 2A. As depicted, the catheter 170C includes a catheter shaft 172C connected to a flexible tip portion 176C that is formed from a looped distal end 174C. The looped distal end 178C includes a plurality of electrodes 178C, only one of which is labeled for ease of illustration, and a catheter shaft 172C further includes a plurality of electrodes 180C, only one of which is labeled.

Figure 6D:
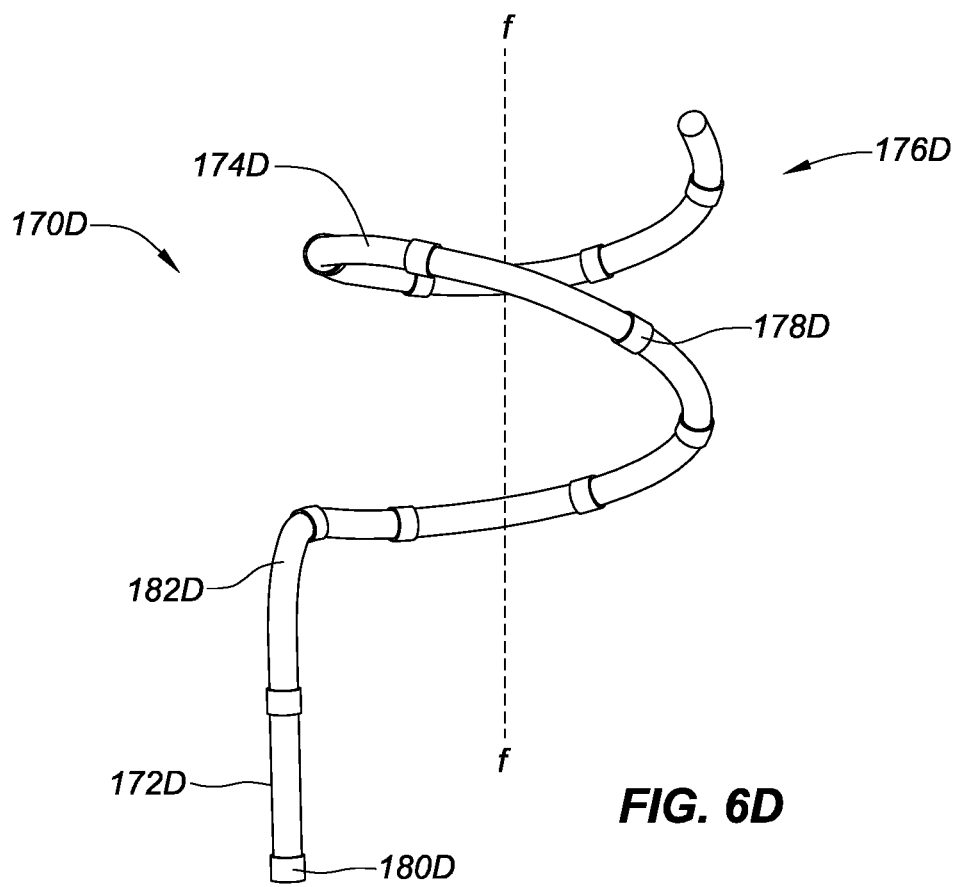

As depicted in FIG. 6D, the catheter shape model can account for a bending of the flexible tip portion 176D of the catheter 170D out of plane, around a curvature of the looped distal end 176D of the catheter 170D. The depicted bending of the flexible tip portion 176D of the catheter 170D is also depicted in relation to arrow 50 of FIG. 2A. As depicted, the catheter 170D includes a catheter shaft 172D connected to a flexible tip portion 176D that is formed from a looped distal end 174D. The looped distal end 178D includes a plurality of electrodes 178D, only one of which is labeled for ease of illustration, and a catheter shaft 172D further includes a plurality of electrodes 180D, only one of which is labeled. The catheter shape model generated for the circular mapping catheter has demonstrated errors smaller than 1 mm when used with a synthetic data set.

In the case of a high-density electrode mapping catheter, such as that depicted in FIG. 2B (e.g., the Advisor™ HD Grid Mapping Catheter, available from Abbott), the catheter was modeled based upon the physical behavior of the catheter shape. To formulate this solution, a finite element was used, and insights were gained about the way forces and constraints were applied to reach the deformed shape. The finite element method (FEM) is a numerical method for solving problems of engineering and mathematical physics. Typical problem areas of interest include structural analysis, heat transfer, fluid flow, mass transport, and electromagnetic potential. The analytical solution of these problems generally requires the solution to boundary value problems for partial differential equations. The finite element method formulation of the problem results in a system of algebraic equations. The method approximates the unknown function over the domain. To solve the problem, it subdivides a large system into smaller, simpler parts that are called finite elements. The simple equations that model these finite elements are then assembled into a larger system of equations that models the entire problem. FEM then uses variational methods from the calculus of variations to approximate a solution by minimizing an associated error function.

A work out of the method can involve (1) dividing the domain of the problem into a collection of subdomains, with each subdomain represented by a set of element equations to the original problem, followed by (2) systematically recombining all sets of element equations into a global system of equations for the final calculation. The global system of equations has known solution techniques and can be calculated from the initial values of the original problem to obtain a numerical answer. Embodiments of the present disclosure can find the forces and positions of application given a set of known deflections on the shape. In some embodiments, a set of solutions can be constructed, each one with small deflections from the last, until the final shape is reached. Using a single FEM solution may not be possible as the construction of the global stiffness matrix assumes known geometry and this geometry may not be calculated using the initial state of the shape.

In some embodiments, a simplified numerical model can be developed based upon the insights gained from the finite element model, which were: catheter shape touching a wall, and forces applied perpendicular to the touching wall. In addition, modeling the catheter stiffness demonstrated that some axes had greater stiffness than others and so some motions were unlikely to occur. For example, the catheter may not be likely to bend in yaw as its moment of inertia can be much higher in yaw, and it can most likely slip from its point of contact. With respect to twist, pure twist may not occur by itself when the catheter shape is unbent, and for this reason, some bend and yaw can be coupled with the twist to keep the shape touching the wall of the heart.

Solving the numerical model can be limited to knowing four parameters that affect the final form of the catheter, which include bending, yaw, twist and curve, as further discussed herein. The equations describing the bending of the catheter along its spine are derived from the Euler Bernoulli beam element. These equations can be used for bend and for yaw with the application of different stiffness for each. The Euler-Bernoulli equation describes the relationship between the deflection of the beam and the applied load. The following formula describes the bending curve as a result of distributed load q.

The Euler-Bernoulli equation describes the relationship between the deflection of the beam and the applied load. The following formula describes the bending curve as a result of distributed load q.

$$\frac{d^2}{dx^2}\left(EI\frac{d^2w}{dx^2}\right) = q$$

The curve w(x) describes the deflection of the beam in the z direction at some position x (recall that the beam is modeled as a one-dimensional object). q is a distributed load, in other words a force per unit length (analogous to pressure being a force per area); it may be a function of x, w, or other variables. In the above equation, E is the elastic modulus and I is the second moment of area of the beam's cross-section. I is calculated with respect to the axis which passes through the centroid of the cross-section and which is perpendicular to the applied loading, explicitly. For a beam whose axis is oriented along x with a loading along Z, the beam's cross-section is in the YZ plane, and the relevant second moment of area is $$I = \iint z^2 \, dy \, dz,$$

Successive derivatives of the deflection w have important physical meanings: dw/dx is the slope of the beam and M is the bending moment in the beam.

$$M = -EI \frac{d^2 w}{dx^2}$$

The Euler Bernoulli theorem can be expanded to a large deflection case, and instead of integration of deflection along the x axis of the beam, the slope can be integrated by sections. The moment can be calculated at each section using the distance from the distal end and a perpendicular force acting upon it.

The theorem used for twist can be torsion of beams in solid mechanics. In the field of solid mechanics, torsion is the twisting of an object due to an applied torque. Torsion is expressed in either the Pascal (Pa), an SI unit for newtons per square meter, or in pounds per square inch (psi) while torque is expressed in newton meters (N·m) or foot-pound force (ft·lbf). In sections perpendicular to the torque axis, the resultant shear stress in this section is perpendicular to the radius.

In non-circular cross-sections, twisting is accompanied by a distortion called warping, in which transverse sections do not remain plane. For shafts of uniform cross-section unrestrained against warping, the torsion can be expressed as:

$$T = \frac{J_T}{r} \tau = \frac{J_T}{\ell} G \varphi$$

where T is the applied torque or moment of torsion in Nm, Tau is the maximum shear stress at the outer surface, $J_T$ is the torsion constant for the section, approximately second moment of area about the neutral axis, r is the distance between the rotational axis and the farthest point in the section (at the outer surface); $\ell$ is the length of the object the torque is being applied to or over; $\varphi$ (phi) is the angle of twist in radians; G is the shear modulus, also called the modulus of rigidity.

The shear stress at a point within a shaft can be expressed as:

$$\tau_{\varphi_z} = \frac{Tr}{J_T}$$

The angle of twist can be found by using:

$$\varphi = \frac{T\ell}{GJ_T}$$

Although a numeric integration in twist is not mandatory for a catheter such as the Advisor™ HD Grid Mapping Catheter, integration steps can be used to integrate the twist as well, because this allows for a change to be made in the torsional stiffness $J_T$ along the spine, achieving higher accuracy of the solution. The Advisor™ HD Grid Mapping Catheter also fits well into a Darboux frame method of modeling the electrodes and curves on the pedal, as discussed below. Pure twist may not exist on the catheter. Forces on the catheter are caused by interface with the walls of the heart and the final shape is the result of a no-slip constraint between a paddle of the high-density electrode mapping catheter and the walls of the heart, so twist can be coupled with bending and/or yaw.

After numeric integration of the catheter shape along its spine, electrode positions and the positions of catheter wires upon this shape can also be calculated. To calculate the electrode positions and the positions of catheter wires upon this shape, the Darboux frame method can be used. In the differential geometry of surfaces, a Darboux frame can be defined as a natural moving frame constructed on a surface. The Darboux frame can be an analog of the Frenet-Serret frame as applied to surface geometry. A Darboux frame exists at any non-umbilic point of a surface embedded in Euclidean space. To use the Darboux frame method for an embedded curve, S can be an oriented surface in three-dimensional Euclidian space $E^3$. The construction of Darboux frames on S first considers frames moving along a curve in S, and then specializes when the curves move in the direction of the principal curvatures. At each point p of an oriented surface, a unit normal vector u(p) may be attached in a unique way, as soon as an orientation has been chosen for the normal at any particular fixed point. If γ(s) is a curve in S, parametrized by arc length, then the Darboux frame of γ can be defined by

| $T(s) = \gamma(s),$ | (the unit tangent) |
| $u(s) = u(\gamma(s)),$ | (the unit normal) |
| $t(s) = u(s) \times T(s),$ | (the tangent normal) |

The triple T, t, u defines a positively oriented orthonormal basis attached to each point of the curve: a natural moving frame along the embedded curve.

Although a numeric integration in twist is not mandatory for a catheter such as the Advisor™ HD Grid Mapping Catheter, integration steps can be used to integrate the twist as well, because this allows for a change to be made in the torsional stiffness $J_T$, along the spine and achieve a higher accuracy of the solution. It also fits well into a Darboux frame method of modeling the electrodes and curves on the pedal, as discussed below. Through observations, pure twist on the catheter has not been identified to exist. For example, forces on the catheter can be caused by interface with the walls of the heart and the final shape is the result of no-slip constraint between a paddle of the high-density electrode mapping catheter and the walls of the heart, so twist can be coupled with bending and often yaw.

A Darboux frame for a curve may not yield a natural moving frame on the surface, since it still depends on an initial choice of tangent vector. To obtain a moving frame on the surface, the Darboux frame of can be compared with its Frenet-Serret frame.

$T(s) = \gamma(s)$, (the unit tangent, as above)

$N(s) = \dfrac{T'(s)}{\|T'(s)\|}$, (the Frenet normal vector)

$B(s) = T(s) \times N(s)$, (the Frenet binormal vector).

Since the tangent vectors are the same in both cases, there is a unique angle $\alpha$ such that a rotation in the plane of N and B produces the pair t and u.

$$\begin{bmatrix} T \\ t \\ u \end{bmatrix} = \begin{bmatrix} 1 & 0 & 0 \\ 0 & \cos\alpha & \sin\alpha \\ 0 & -\sin\alpha & \cos\alpha \end{bmatrix} \begin{bmatrix} T \\ N \\ B \end{bmatrix}$$

Taking a differential, and applying the Frenet-Serret formulas yields $$d\begin{bmatrix} T \\ t \\ u \end{bmatrix} = \begin{bmatrix} 0 & \kappa\cos\alpha\,ds & -\kappa\sin\alpha\,ds \\ -\kappa\cos\alpha\,ds & 0 & \tau ds + d\alpha \\ \kappa\sin\alpha\,ds & -\tau ds - d\alpha & 0 \end{bmatrix} \begin{bmatrix} T \\ t \\ u \end{bmatrix} =$$

$$\begin{bmatrix} 0 & \kappa_g ds & \kappa_n ds \\ -\kappa_g ds & 0 & \tau_r ds \\ -\kappa_n ds & -\tau_r ds & 0 \end{bmatrix} \begin{bmatrix} T \\ t \\ u \end{bmatrix}$$

where $\kappa_g$ is the geodesic curvature of the curve, $\kappa_n$ is the normal curvature of the curve, and $\tau_{rj}$ is the relative torsion (also called geodesic torsion) of the curve. Using the above solution, a catheter shape can be calculated using numerical integration along the spine of the catheter, working in bend, yaw and twist, and a final catheter shape was obtained using the Darboux frame method. Calculation of electrode positions and catheter frame curves can be made by orthogonal projection of the two-dimensional catheter shape and electrodes onto the deformed Darboux frame to provide a catheter shape model.

Figure 7A:
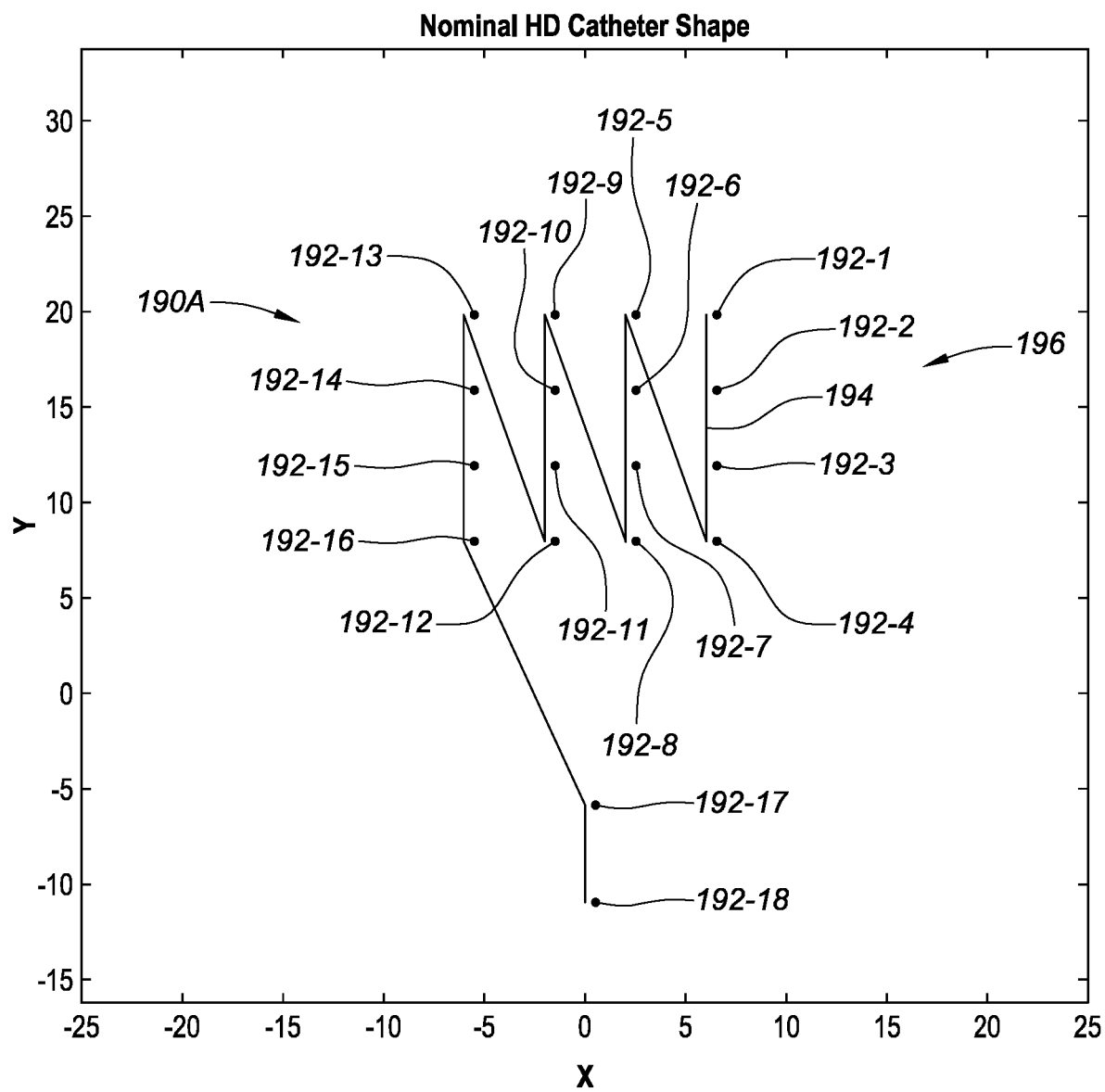
FIG. 7A depicts an orthogonal projection of a two-dimensional catheter shape, in accordance with embodiments of the present disclosure.

The orthogonal projection 190A is depicted in FIG. 7A. As depicted, the orthogonal projection 190A of the two-dimensional catheter shape includes electrode locations 192-1, 192-2, ..., 192-16, hereinafter collectively referred to as electrode locations 192, and a distance 194 between each one of the electrode locations 192. As depicted, the distance between each one of the electrode locations 192 along the flexible tip portion 196 along the spine of the catheter remains the same, which is representative of the behavior of the physical catheter. However, spacing between the electrode locations 192-1, 192-2, 192-3, 192-4 and electrode locations 192-13, 192-14, 192-15, 192-16 located on the sides of the flexible tip portion 196 do not remain the same, because a distance between the sides of the flexible tip portion 196 can change with respect to how much force is applied to either side. For example, the flexible tip portion can experience twist and/or curve, causing a distance between the electrodes disposed on either side of the flexible tip portion 196 to change. As depicted, the electrode locations 192-17, 192-18 are associated with electrodes disposed on a shaft of the catheter and are included in the orthogonal projection.

Figure 7B:
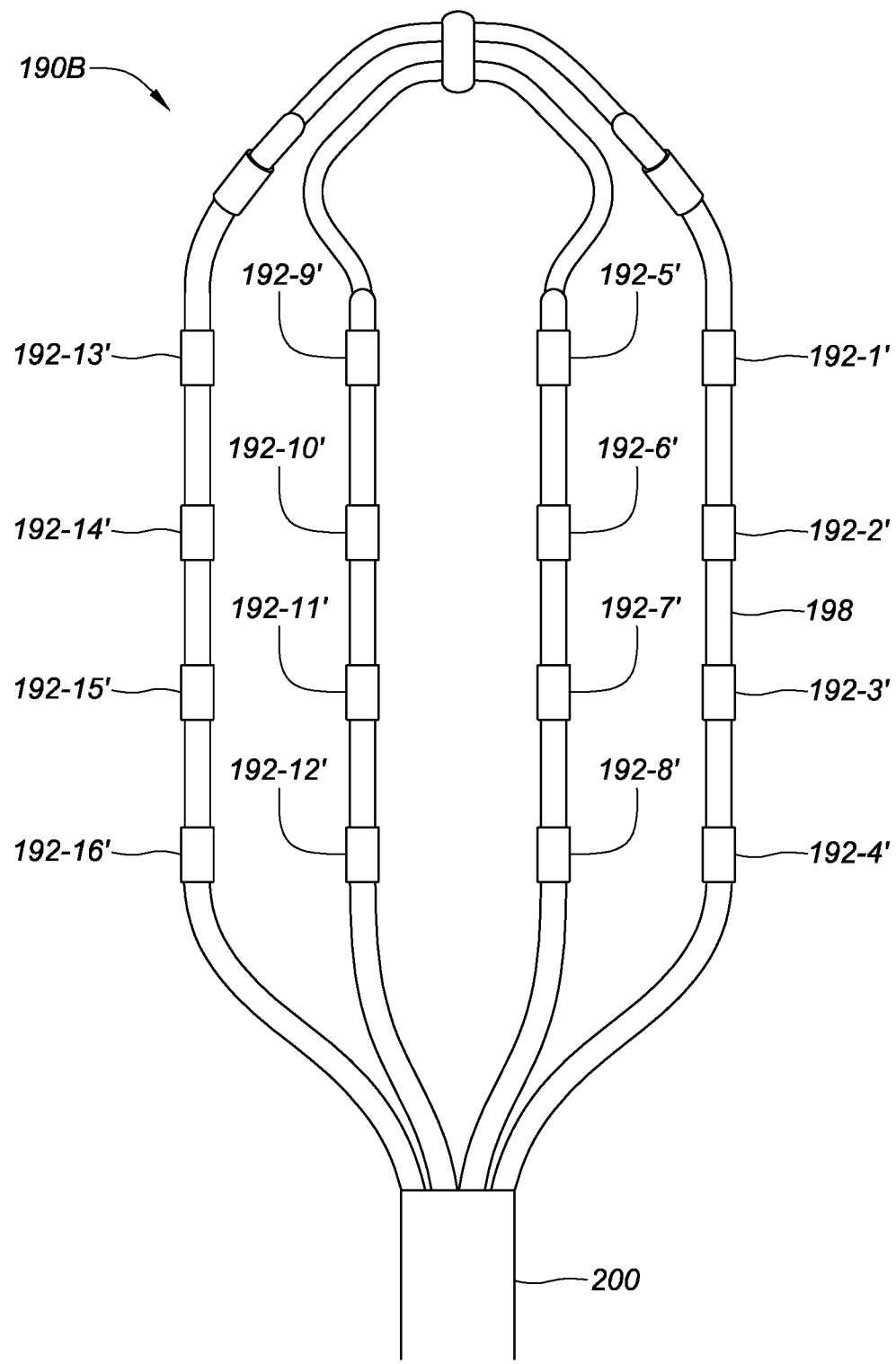
FIG. 7B depicts a final catheter shape model, where the orthogonal projection depicted in FIG. 7A has been projected to provide the final catheter shape model, in accordance with embodiments of the present disclosure.

FIG. 7B depicts a final catheter shape model 190B where the orthogonal projection 190A depicted in FIG. 7A has been projected onto the Darboux frame 198, to provide the final catheter shape model 190B. Although not illustrated, shaft electrode locations 192-17, 192-18 depicted in FIG. 7A can also be projected onto the Darboux frame 198. The catheter shape model 190B can be used to model a bending, yaw, twist, and curve of the physical catheter, as further discussed herein.

Figure 8A:
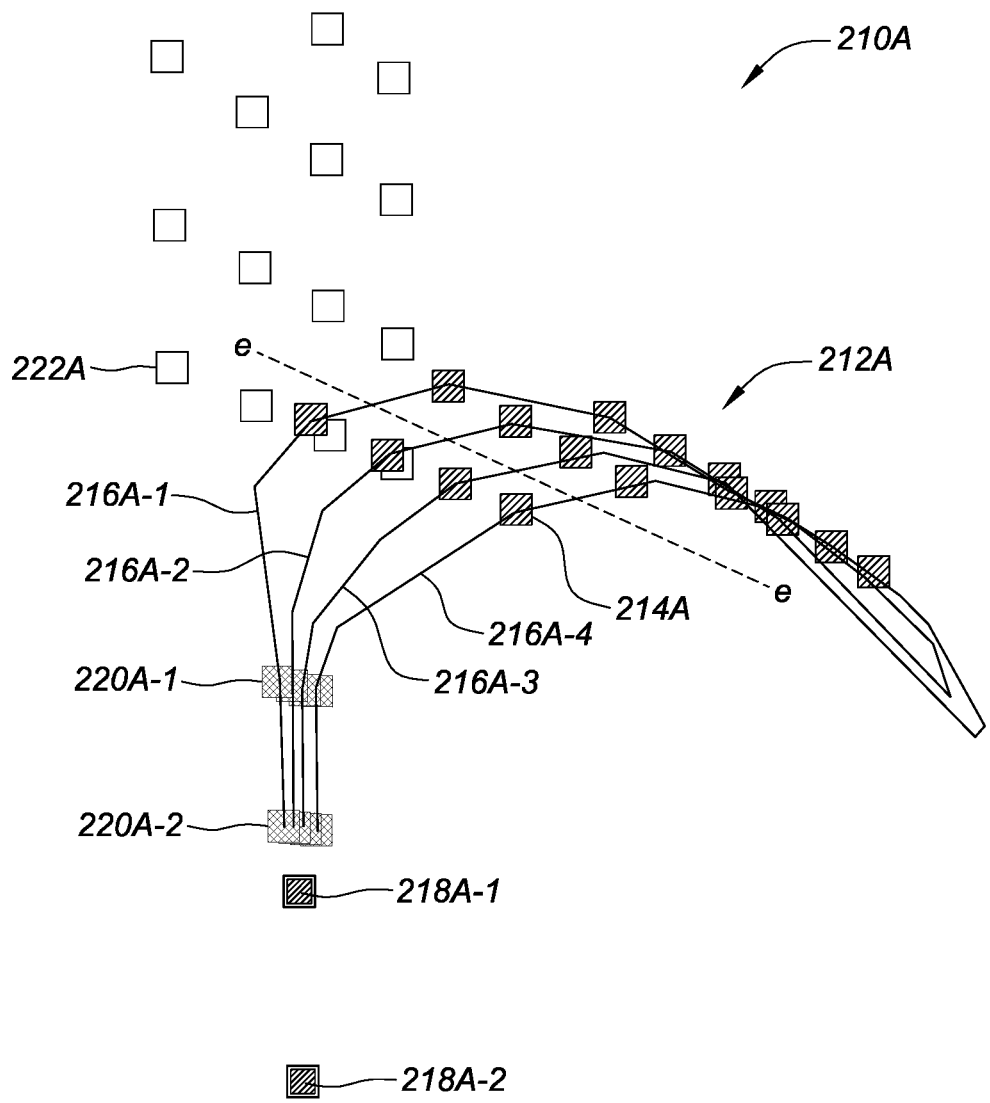
FIGS. 8A to 8D depict the parameters used to define a catheter shape model of a high-density electrode mapping catheter, in accordance with embodiments of the present disclosure.

FIGS. 8A to 8D depict the parameters used to define a catheter shape model of a high-density electrode mapping catheter. As depicted in FIG. 8A, the catheter shape model 210A can account for a bending of the flexible tip portion 212A of the catheter around the x-axis, defined by line e-e. The depicted bending of the flexible tip portion 212A of the catheter is also depicted in relation to arrow 112a and 112b of FIG. 2B. As depicted, the catheter shape model 210A includes a flexible tip portion 212A that includes a plurality of electrode locations 214A. Although the catheter shape model 210A includes the plurality of electrode locations 214A, only electrode location 214A has been labeled for ease of illustration.

The catheter shape model 210A also includes frame curves 216A-1, 216A-2, 216A-3, 216A-4 projected through the Darboux frame method. The catheter shape model 210A is also depicted as including catheter shaft electrode locations 218A-1, 218A-2. The catheter shaft electrode locations 218A-1, 218A-2, in some embodiments can be determined through magnetic position sensor locations 220A-1, 220A-2, also depicted in the catheter shape model 210A. The magnetic position sensor locations 220A-1, 220A-2 can be obtained through a magnetic position sensor disposed on a shaft of the catheter depicted in the catheter shape model 210A. For reference, undeflected electrode positions 222A are depicted as boxes to show the difference in deflection between an undeflected state, represented by the undeflected electrode positions 222A and the electrode locations 214A included in the catheter shape model 210A that reflects a bending of the flexible tip portion 212A.

Figure 8B:
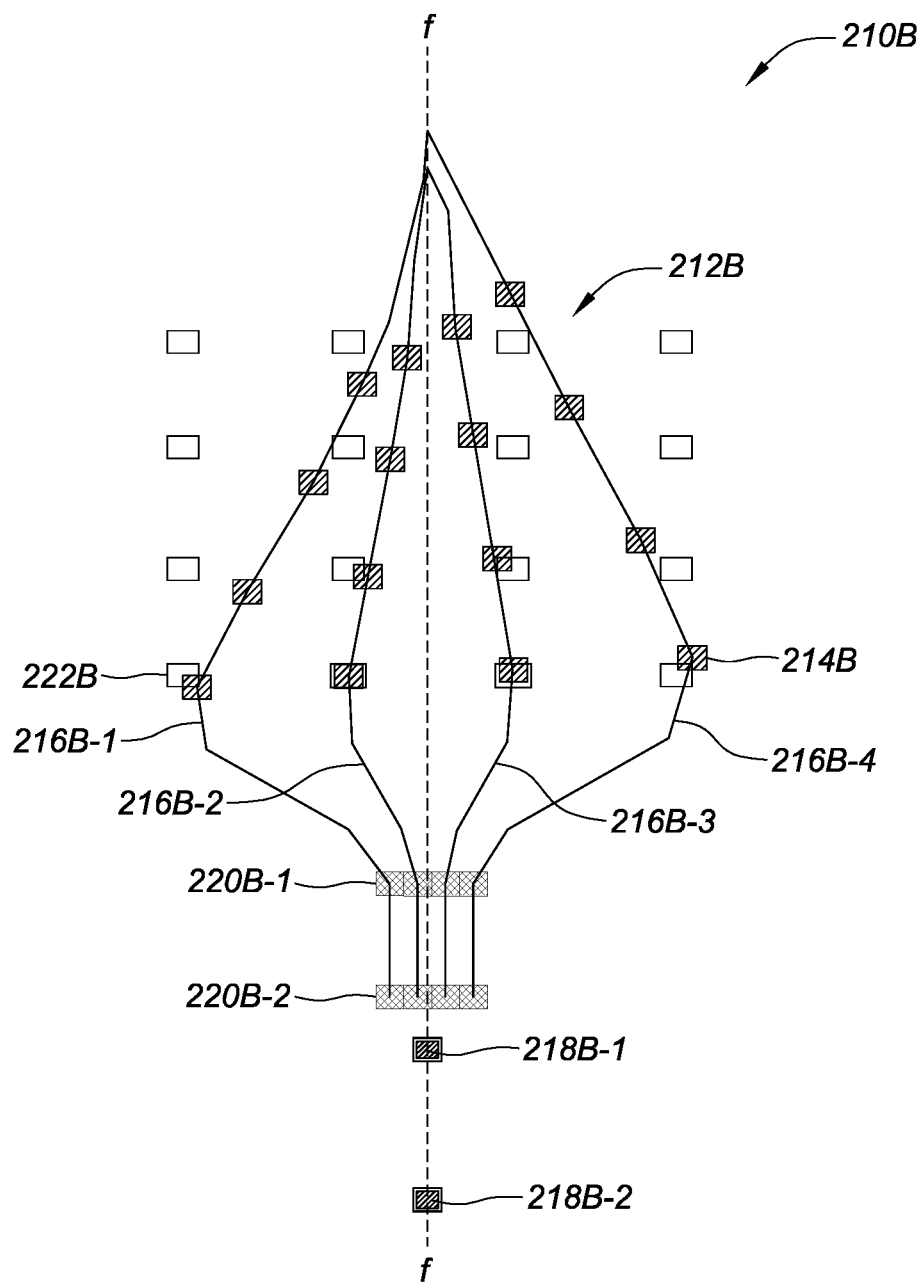

As depicted in FIG. 8B, the catheter shape model 210B can account for a twisting of the flexible tip portion 212B of the catheter along a spine of the catheter and around the y-axis, defined by line f-f. The bending of the flexible tip portion 212B of the catheter is also depicted in relation to arrow 114a and 114b of FIG. 2B. As depicted, the catheter shape model 210B includes a flexible tip portion 212B that includes a plurality of electrode locations 214B. Although the catheter shape model 210B includes the plurality of electrode locations 214B, only electrode location 214B has been labeled for ease of illustration.

The catheter shape model 210B also includes frame curves 216B-1, 216B-2, 216B-3, 216B-4 projected through the Darboux frame method. The catheter shape model 210B is also depicted as including catheter shaft electrode locations 218B-1, 218B-2. The catheter shaft electrode locations 218B-1, 218B-2, in some embodiments, can be determined through magnetic position sensor locations 220B-1, 220B-2, also depicted in the catheter shape model 210B. The magnetic position sensor locations 220B-1, 220B-2 can be obtained through a magnetic position sensor disposed on a shaft of the catheter depicted in the catheter shape model 210B. For reference, undeflected electrode positions 222B are depicted as boxes to show the difference in deflection between an undeflected state, represented by the undeflected electrode positions 222B and the electrode locations 214B included in the catheter shape model 210B that reflects a twisting of the flexible tip portion 212B.

Figure 8C:
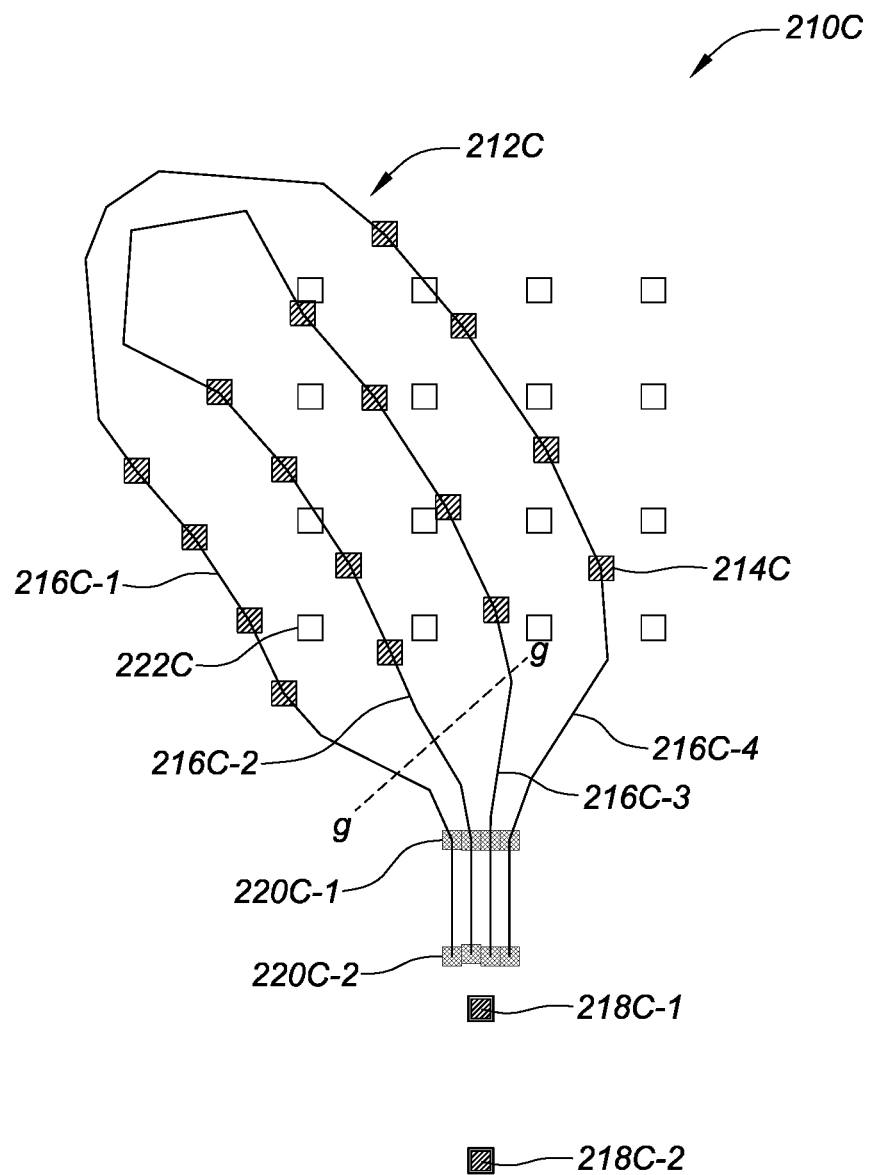

As depicted in FIG. 8C, the catheter shape model 210C can account for a yaw of the flexible tip portion 212C of the catheter around the z-axis, defined by line g-g. The depicted yaw of the flexible tip portion 212C of the catheter is also depicted in relation to arrow 115a and 115b of FIG. 2B. As depicted, the catheter shape model 210C includes a flexible tip portion 212C that includes a plurality of electrode locations 214C. Although the catheter shape model 210C includes the plurality of electrode locations 214C, only electrode location 214C has been labeled for ease of illustration.

The catheter shape model 210C also includes frame curves 216C-1, 216C-2, 216C-3, 216C-4 projected through the Darboux frame method. The catheter shape model 210C is also depicted as including catheter shaft electrode locations 218C-1, 218C-2. The catheter shaft electrode locations 218C-1, 218C-2, in some embodiments, can be determined through magnetic position sensor locations 220C-1, 220C-2, also depicted in the catheter shape model 210C. The magnetic position sensor locations 220C-1, 220C-2 can be obtained through a magnetic position sensor disposed on a shaft of the catheter depicted in the catheter shape model 210C. For reference, undeflected electrode positions 222C are depicted as boxes to show the difference in deflection between an undeflected state, represented by the undeflected electrode positions 222C and the electrode locations 214C included in the catheter shape model 210C that reflects a yaw of the flexible tip portion 212C.

Figure 8D:
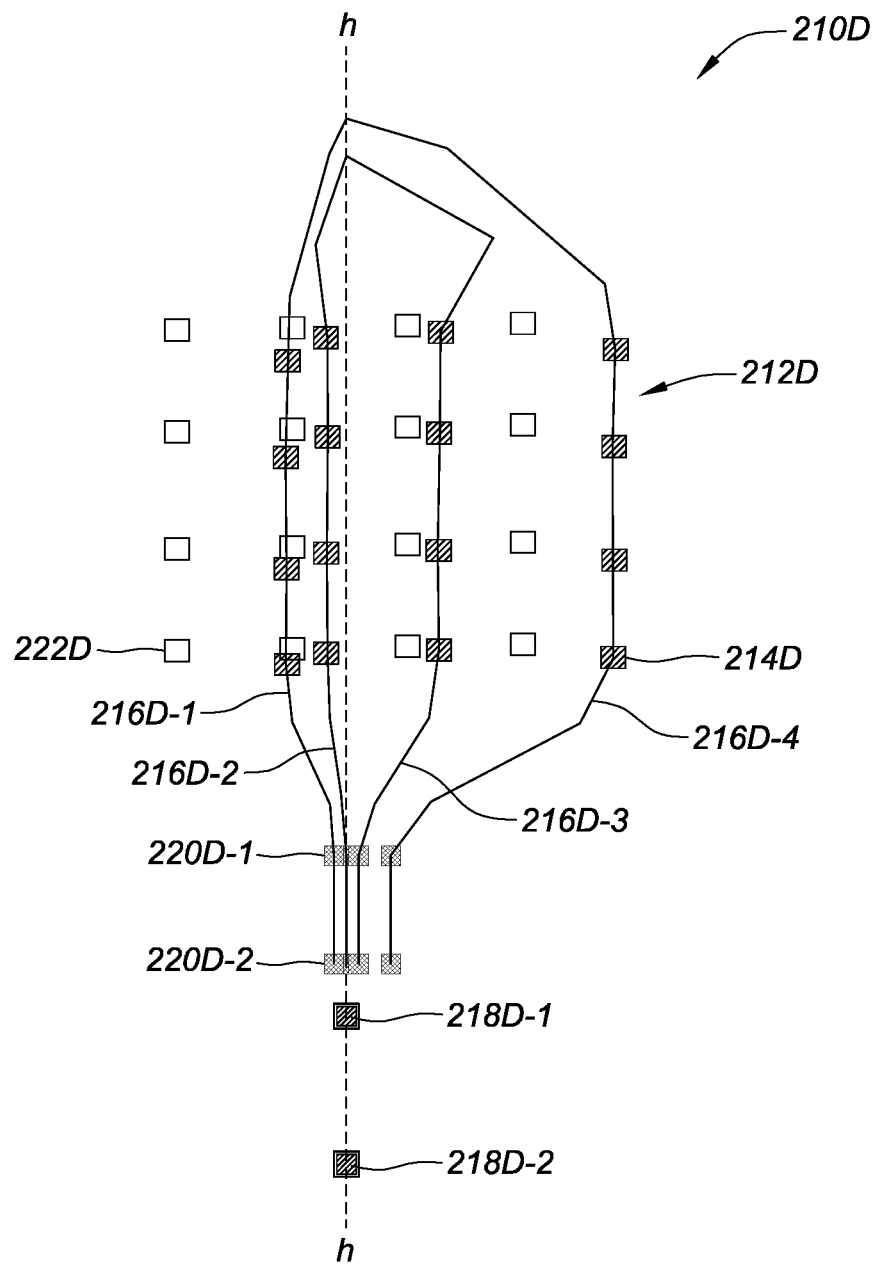

As depicted in FIG. 8D, the catheter shape model 210D can account for a curve of the flexible tip portion 212D of the catheter around the z-axis, defined by line h-h. The depicted curve of the flexible tip portion 212D of the catheter is also depicted in relation to arrow 113a and 113b of FIG. 2B. As depicted, the catheter shape model 210D includes a flexible tip portion 212D that includes a plurality of electrode locations 214D. Although the catheter shape model 210D includes the plurality of electrode locations 214D, only electrode location 214D has been labeled for ease of illustration. The catheter shape model 210D also includes frame curves 216D-1, 216D-2, 216D-3, 216D-4 projected through the Darboux frame method.

The catheter shape model 210D is also depicted as including catheter shaft electrode locations 218D-1, 218D-2. The catheter shaft electrode locations 218D-1, 218D-2, in some embodiments, can be determined through magnetic position sensor locations 220D-1, 220D-2, also depicted in the catheter shape model 210D. The magnetic position sensor locations 220D-1, 220D-2 can be obtained through a magnetic position sensor disposed on a shaft of the catheter depicted in the catheter shape model 210D. For reference, undeflected electrode positions 222D are depicted as boxes to show the difference in deflection between an undeflected state, represented by the undeflected electrode positions 222D and the electrode locations 214D included in the catheter shape model 210D that reflects a yaw of the flexible tip portion 212D.

With further reference to FIG. 1, embodiments of the present disclosure can include a computer system 20 that is configured to determine a shape of a catheter (e.g., catheter 13). In some embodiments, the system 20 can include computer-readable instructions that are executable by the processing resource 32 to receive a plurality of raw impedance measurements from a plurality of electrodes 17 disposed on a flexible tip portion of the catheter 13. As discussed herein, embodiments of the present disclosure can use raw impedance measurements received from the plurality of electrodes 17, which can be subject to shift and drift. Use of the raw impedance measurements can reduce an amount of processing resources that are used to refine the impedance data, which can be used by other methods that determine a catheter shape.

In some embodiments, instructions can be executed to receive a magnetic position measurement from a magnetic position sensor, not depicted in FIG. 1, disposed on a shaft of the catheter 13. An angle between each of the plurality of electrodes disposed on the flexible tip portion of the catheter can be determined, based on the raw impedance measurements received from the plurality of electrodes. Depending on a type and/or amount of deflection of the flexible tip portion of the catheter 13, angles between the electrodes can change in relation to one another, which can provide an indication of a particular shape of the flexible tip portion. Although shift and/or drift may be associated with the impedance measurements, the electrostatic field in which the electrodes are located can be generally uniform, such that the electrostatic field does not have a particularly different effect on one electrode versus another electrode in the domain size of the flexible tip portion. For example, if shift and/or drift occurs, the effect can be relatively uniform on all of the plurality of different electrodes, which can allow for an accurate calculation of the shape of the flexible tip portion, based on a relationship (e.g., angle) between each one of the electrodes.

In some embodiments, even though shift and/or draft may affect each impedance measurement in a generally uniform way, the impedance measurements can still be subject to shift and/or drift. Accordingly, embodiments of the present disclosure can shift a determined location of the flexible tip portion of the catheter based on the magnetic position sensor measurement. The magnetic position sensor, which can be disposed in the catheter shaft, stays within a known position and/or orientation of the flexible tip portion and thus also stays within a known position and/or orientation of the electrodes disposed on the flexible tip portion. Thus, the magnetic position sensor measurement can serve as a reference point to shift the determined location of the flexible tip portion.

In some embodiments, a location of the shaft of the catheter can be determined based on the magnetic position sensor measurement. The determined location of the flexible tip portion of the catheter can then be shifted based on the magnetic position sensor measurement and/or the determined location of the shaft of the catheter. In an example, the determined location of the flexible tip portion of the catheter is shifted to align the determined location of the flexible tip portion with the determined location of the shaft of the catheter. In some embodiments, the shape of the catheter, as a whole (e.g., including the shaft of the catheter and the flexible tip portion) can be determined using the shifted location of the flexible tip portion of the catheter. In an example, the determined shape of the catheter can be displayed on a display 23 (e.g., graphical user interface) to a physician performing a therapeutic and/or diagnostic operation on a patient.

Embodiments are described herein of various apparatuses, systems, and/or methods. Numerous specific details are set forth to provide a thorough understanding of the overall structure, function, manufacture, and use of the embodiments as described in the specification and depicted in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for determination of a catheter shape has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. A method comprising:
    receiving, by a processor, a plurality of raw impedance measurements from a plurality of electrodes disposed on a flexible tip portion of a catheter configured to be inserted into a patient;
    receiving, by a processor, a magnetic position measurement from a magnetic position sensor disposed on a shaft of the catheter;
    determining, by a processor, an angle between each of the plurality of electrodes disposed on the flexible tip portion of the catheter, using the raw impedance measurements received from the plurality of electrodes;
    predicting, by a processor, a shape of the flexible tip portion of the catheter, using the determined angle between each of the plurality of electrodes disposed on the flexible tip portion of the catheter;
    determining, by a processor, a shape of the catheter, using the magnetic position measurement and the predicted shape of the flexible tip portion; and
    generating, by a processor, a visual representation of the determined shape of the catheter for display on a display device.

2. The method of claim 1, wherein a shape model of the flexible tip portion factors in bending, yaw, curvature, and twist of the flexible tip portion.

3. The method of claim 1, further comprising receiving an orientation measurement from the magnetic position sensor disposed on the catheter.

4. The method of claim 3, wherein determining the shape of the catheter includes shifting the predicted shape of the flexible tip portion of the catheter in relation to the shaft of the catheter, based on the position and orientation measurements received from the magnetic position sensor.

5. The method of claim 1, further comprising filtering the raw impedance measurements received from the plurality of electrodes disposed on the flexible tip portion of the catheter.

6. The method of claim 1, wherein the method includes transforming the raw impedance measurements from an impedance domain to a magnetic domain through use of a rigid body transformation, wherein constraints of the rigid body transformation include known distances between the electrodes on the flexible tip portion.

7. The method of claim 6, wherein the method further comprises:
    determining a local field scaling associated with the raw impedance measurements; and
    transforming the raw impedance measurements into magnetic positions by scaling the raw impedance measurements based on the local field scaling.

8. The method of claim 7, wherein the local field scaling is constant over the flexible tip portion of the catheter.

9. The method of claim 1, wherein:
    the catheter is a mapping catheter; and
    the flexible tip portion of the catheter on which the plurality of electrodes are disposed is circular in shape.

10. The method of claim 1, wherein:
    the catheter is a mapping catheter; and
    the flexible tip portion of the catheter on which the plurality of electrodes are disposed is paddle shaped.

11. The method of claim 1, further comprising predicting locations of each of the plurality of electrodes disposed on the flexible tip portion of the catheter.

12. A system for determining a shape of a catheter configured to be positioned within a patient, the system comprising:
an electronic control unit including a processor and memory storing instructions executable by the processor to:
receive a plurality of raw impedance measurements from a plurality of electrodes disposed on a flexible tip portion of the catheter;
receive a magnetic position measurement from a magnetic position sensor disposed on a shaft of the catheter;
determine an angle between each of the plurality of electrodes disposed on the flexible tip portion of the catheter, using the raw impedance measurements received from the plurality of electrodes;
predict a shape of the flexible tip portion of the catheter, using the determined angle between each of the plurality of electrodes disposed on the flexible tip portion of the catheter;
shift a determined location of the flexible tip portion of the catheter using the magnetic position sensor measurement; and
determine the shape of the catheter using the shifted location of the flexible tip portion of the catheter; and
generate a visual representation of the determined shape of the catheter and provide as an output to a display.

13. The system of claim 12, further comprising instructions executable by the processor to determine a location of the shaft of the catheter based on the magnetic position sensor measurement.

14. The system of claim 13, wherein the determined location of the flexible tip portion of the catheter is shifted to align the determined location of the flexible tip portion with the determined location of the shaft of the catheter.

15. The system of claim 12, further comprising instructions executable by the processor to:
determine a local field scaling associated with the raw impedance measurements; and
transform the raw impedance measurements into magnetic positions by scaling the raw impedance measurements based on the local field scaling.

* * * * *